United States Patent [19]

Mick et al.

[11] Patent Number: 5,355,893
[45] Date of Patent: Oct. 18, 1994

[54] VITAL SIGNS MONITOR

[76] Inventors: Peter R. Mick, 4 Stonybrook Trail, Kinnelon, N.J. 07405; Donald C. Beck, 18 Woodglen Way, Boonton, N.J. 07005

[21] Appl. No.: 120,183

[22] Filed: Sep. 13, 1993

Related U.S. Application Data

[63] Continuation-in-part of Ser. No. 864,312, Apr. 6, 1992, abandoned.

[51] Int. Cl.⁵ .......................... A61B 5/08; A61B 5/097
[52] U.S. Cl. .................................. 128/719; 128/725; 128/664
[58] Field of Search ............... 128/633, 634, 637, 664, 128/665, 670, 671, 689, 691, 713, 716, 718, 719, 725, 736, 204.21, 724

[56] References Cited

U.S. PATENT DOCUMENTS

| | | | |
|---|---|---|---|
| 3,675,640 | 7/1972 | Gatts | 128/671 |
| 3,991,304 | 11/1976 | Hillsman | 128/720 |
| 4,067,320 | 1/1978 | Olsson et al. | 128/719 |
| 4,248,245 | 2/1981 | Kempin | 128/724 |
| 4,270,547 | 6/1981 | Steffen et al. | 128/736 |
| 4,366,821 | 1/1983 | Wittmaier et al. | 128/724 |
| 4,383,534 | 5/1983 | Peters | 128/671 |
| 4,480,190 | 10/1984 | Burough et al. | 250/343 |
| 4,598,700 | 7/1986 | Tamm | 128/689 X |
| 4,756,670 | 7/1988 | Arai | 128/719 |
| 4,777,963 | 10/1988 | McKenna | 128/724 |
| 4,883,051 | 11/1989 | Westenskow et al. | 128/204.21 |
| 4,909,259 | 3/1990 | Tehrani | 128/670 |
| 4,998,018 | 3/1991 | Kurahashi et al. | 128/719 |
| 5,069,220 | 12/1991 | Casparie et al. | 128/719 |
| 5,094,246 | 3/1992 | Rusz et al. | 128/716 |
| 5,095,913 | 3/1992 | Yelderman et al. | 128/633 |

Primary Examiner—Lee S. Cohen
Assistant Examiner—Samuel Gilbert
Attorney, Agent, or Firm—Alfred C. Hill

[57] ABSTRACT

A vital signs monitor comprising a first device capable of being disposed at a selected location on a patient to pass at least exhaled gases therethrough; a second device coupled to the first device to perform a plurality of resistive measurements of certain predetermined parameters of the exhaled gases and a plurality of optical absorption measurements of other predetermined parameters of the exhaled gases; and a third device coupled to the second device responsive to the plurality of resistive measurements and the plurality of optical absorption measurements to provide individual read outs of at least a value of carbon dioxide in the exhaled gases, a value of tidal volume of the exhaled gases and a value of a respiration rate of the patient.

23 Claims, 11 Drawing Sheets

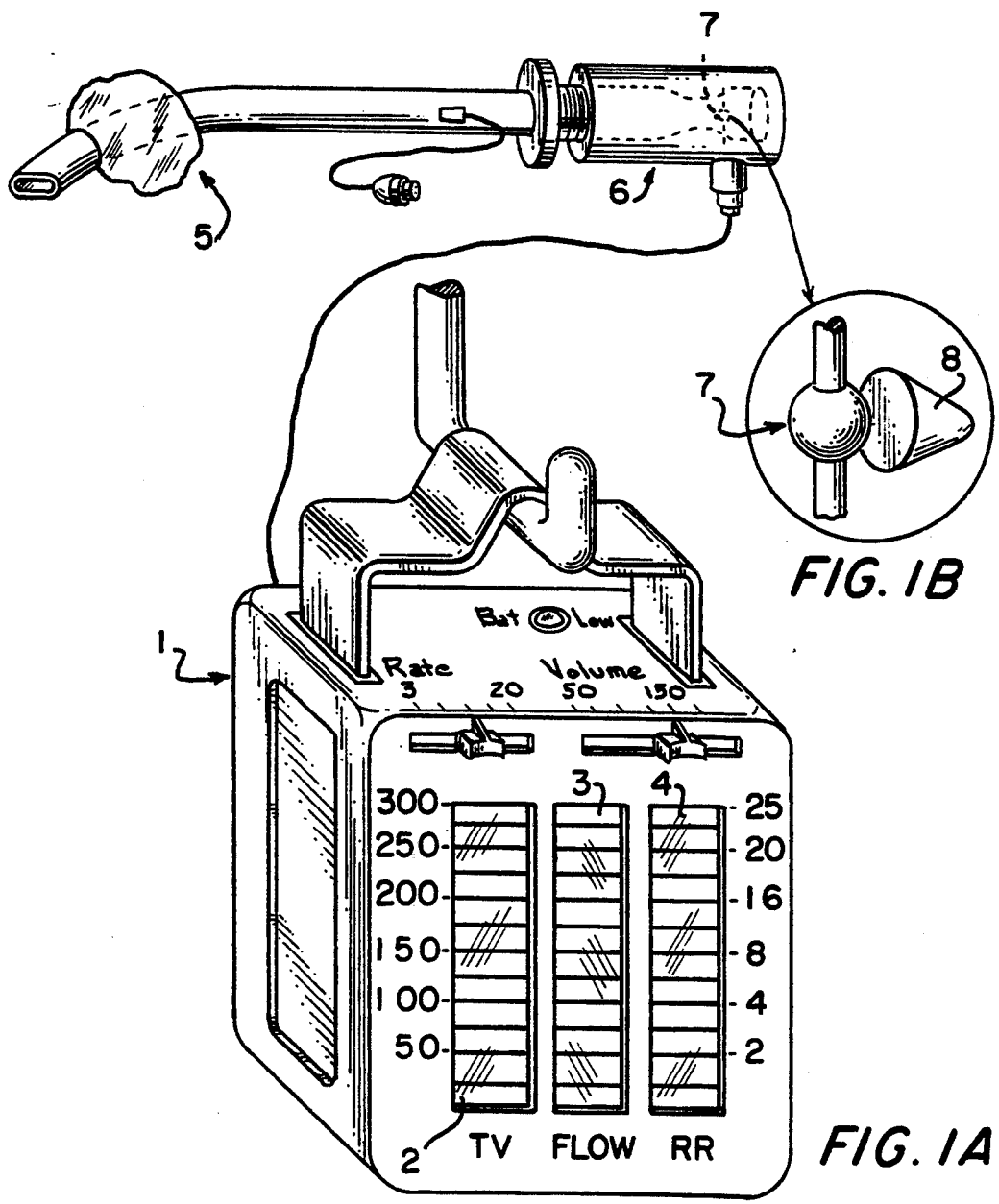
FIG. 1B
FIG. 1A
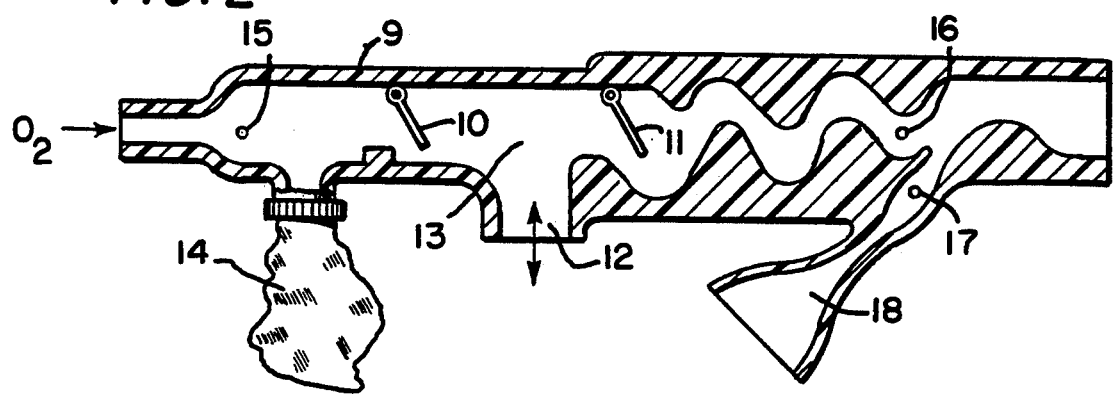
FIG. 2

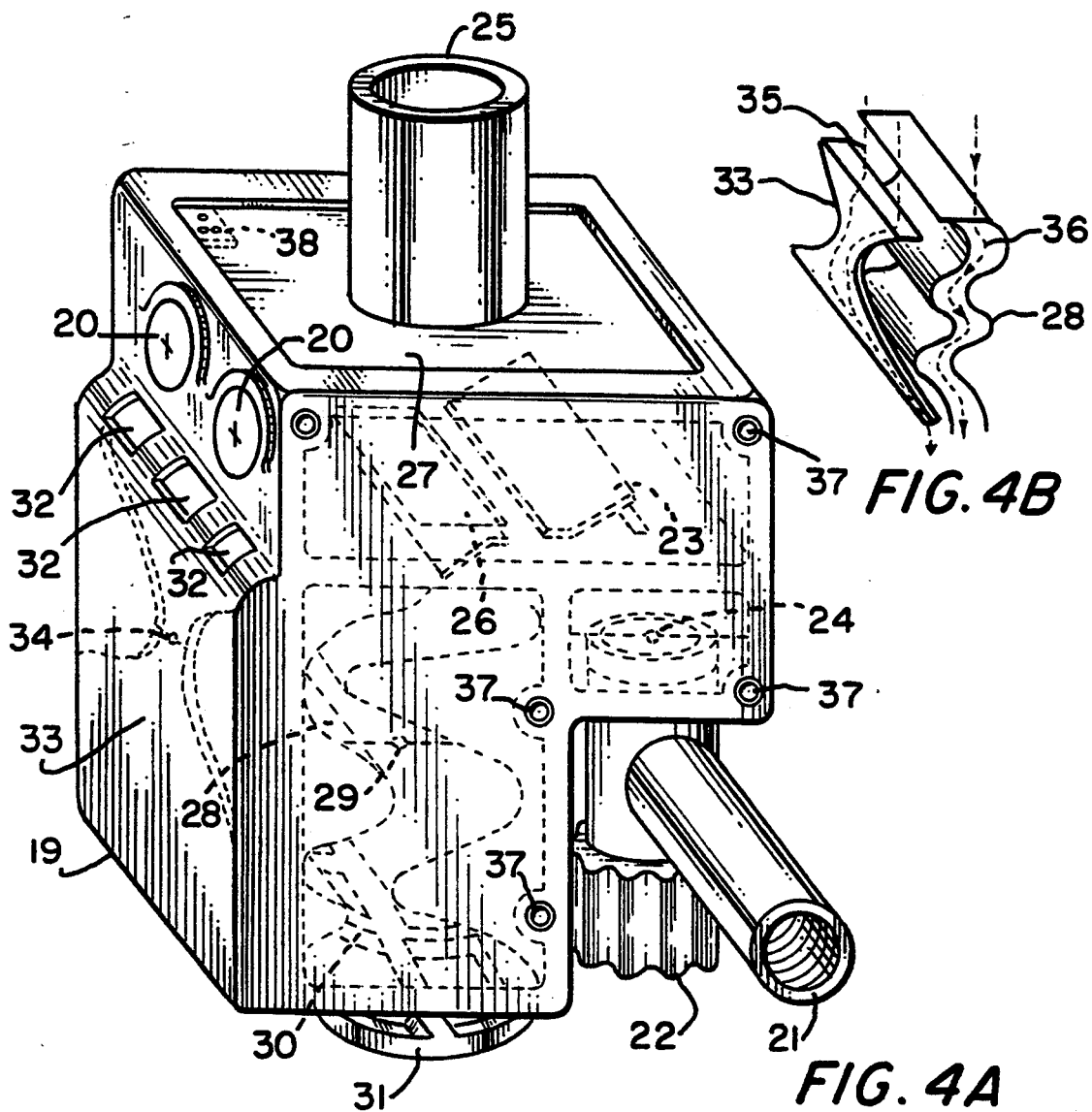
FIG. 4B
FIG. 4A
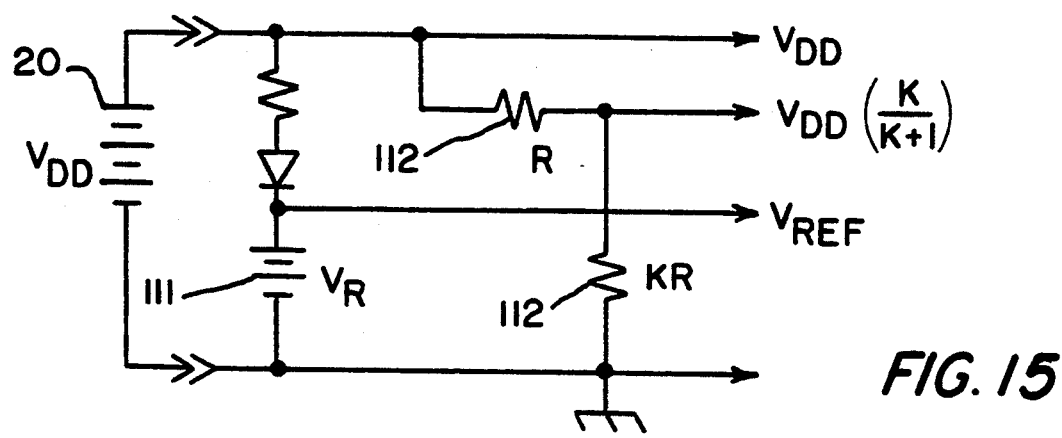
FIG. 15

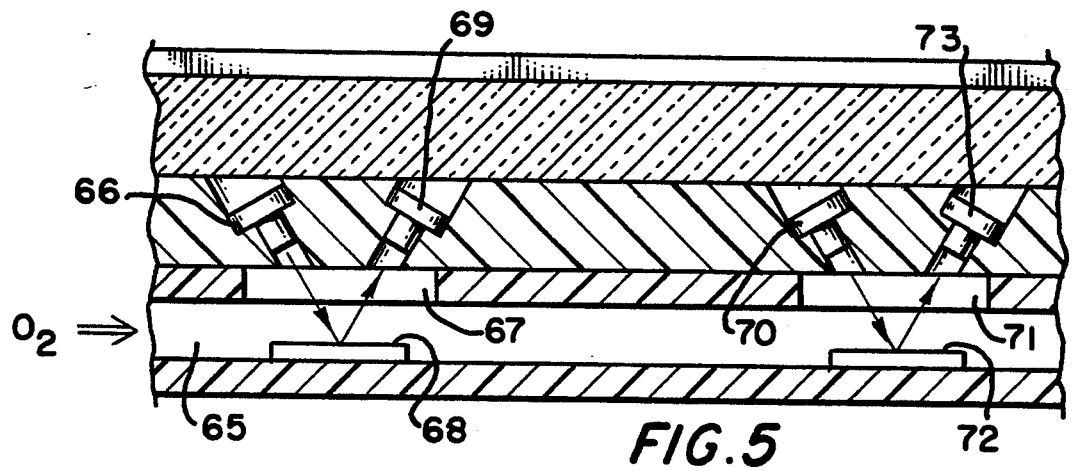
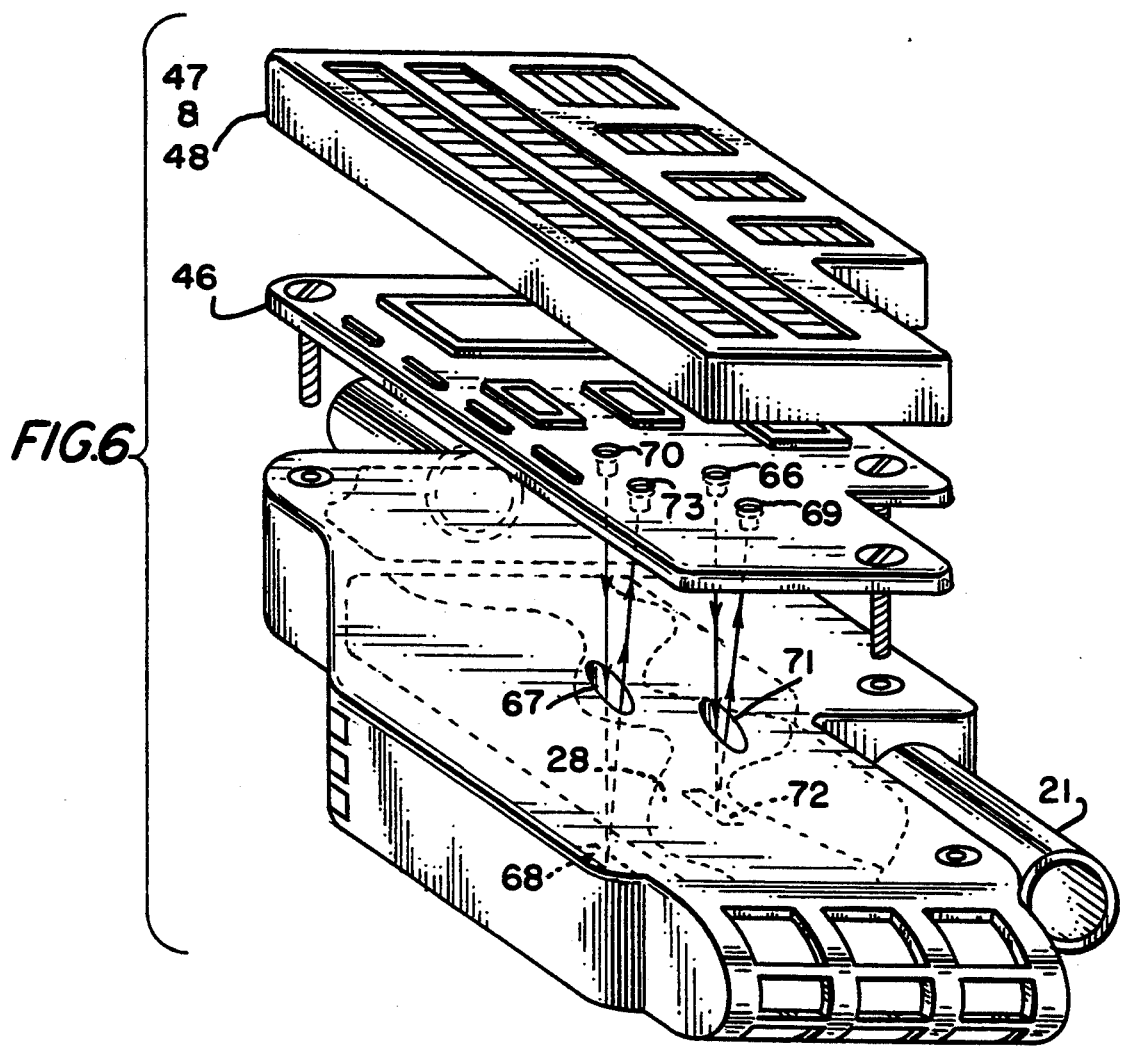

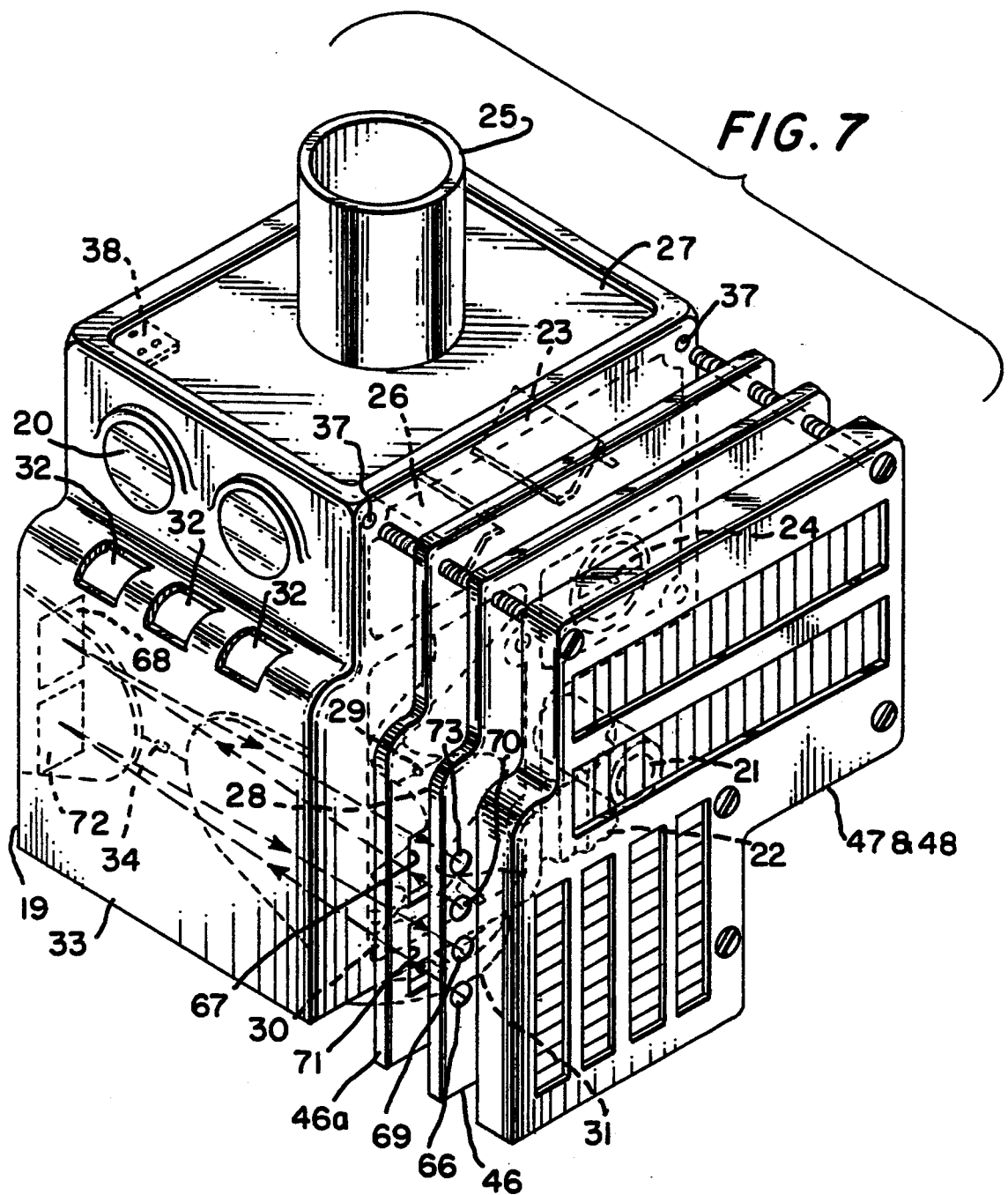

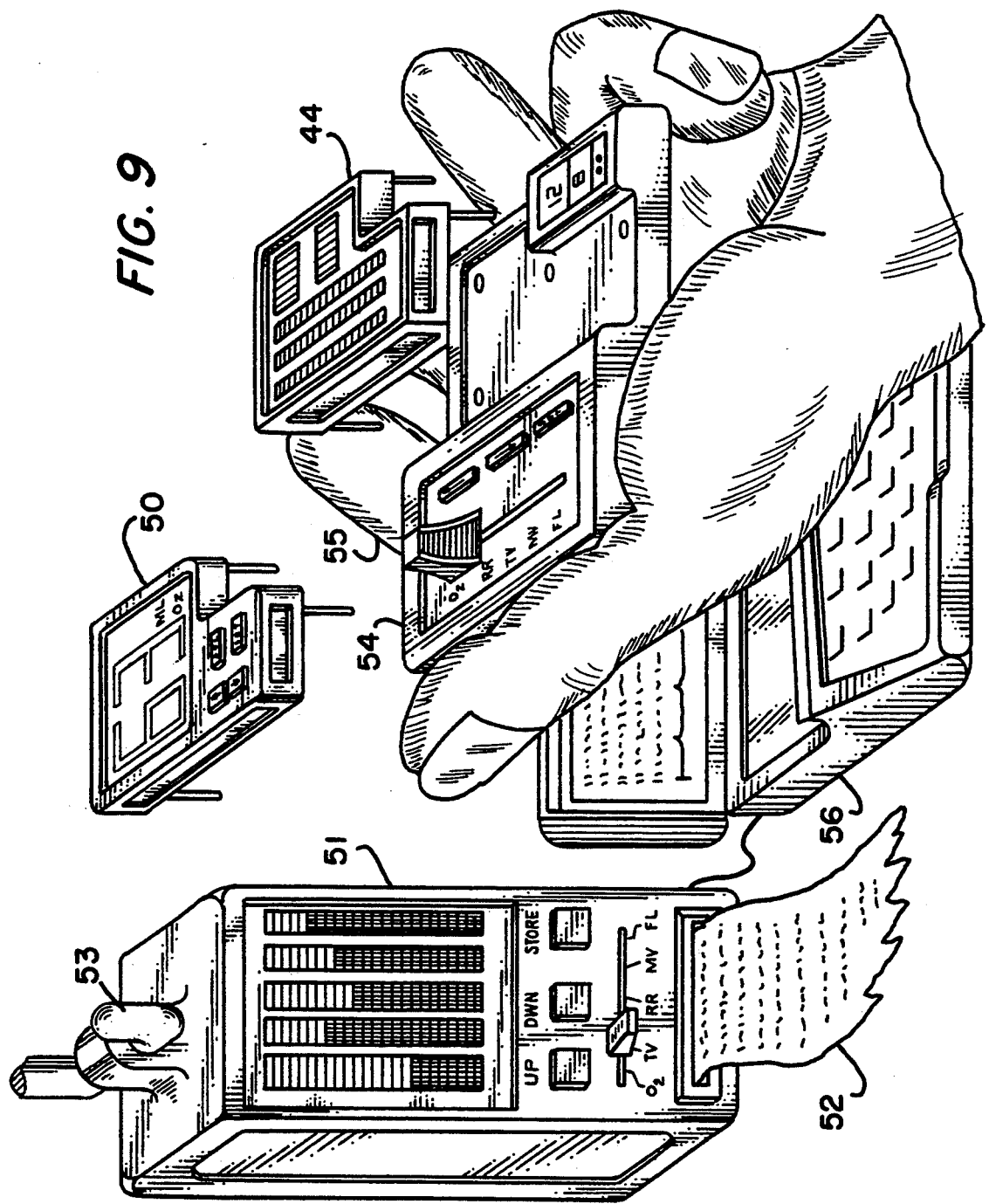

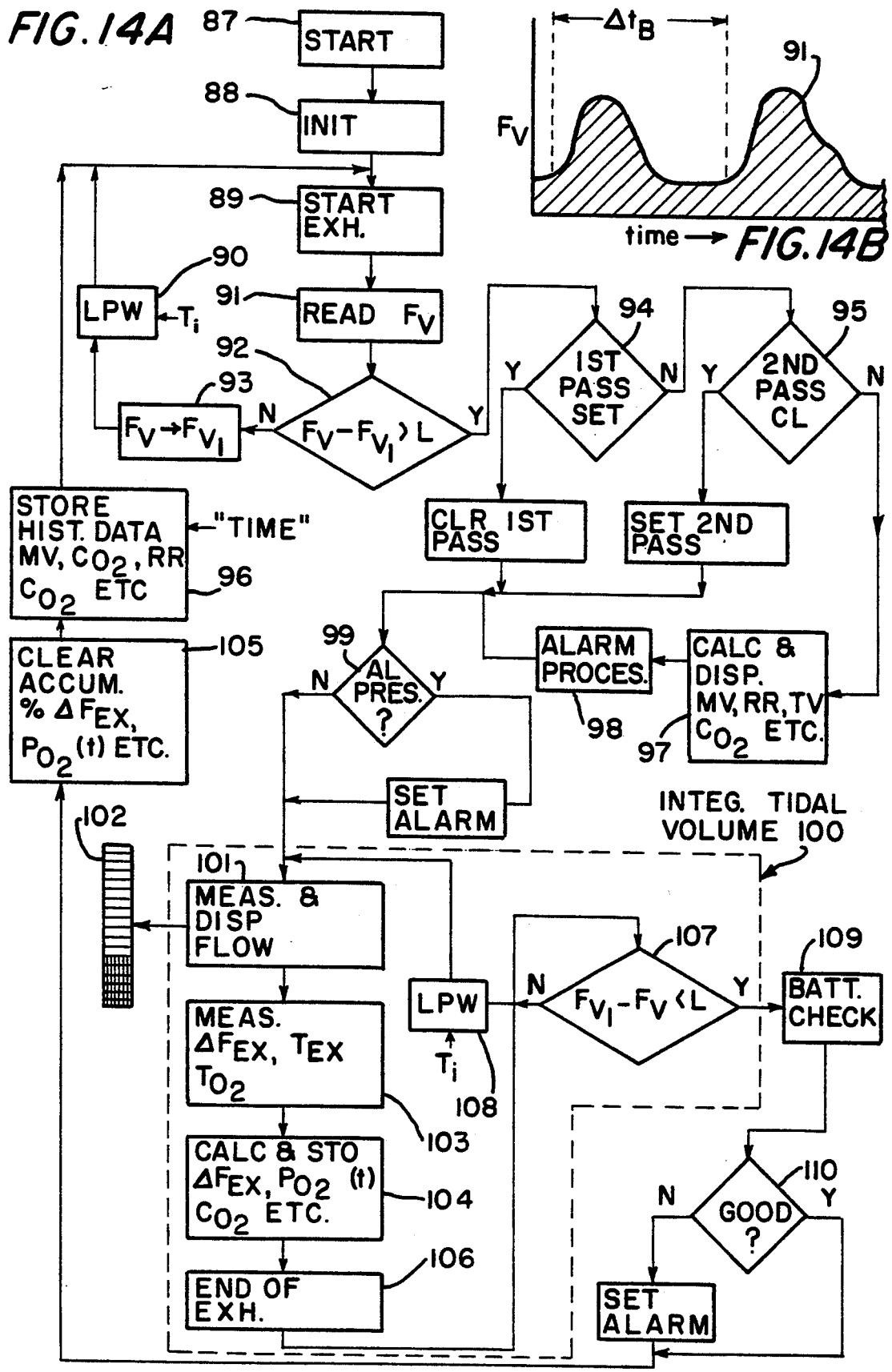

VITAL SIGNS MONITOR

CROSS-REFERENCE TO RELATED APPLICATION

The present invention is a continuation-in-part application of application Ser. No. 864,312, filed Apr. 6, 1992, now abandoned.

BACKGROUND OF THE INVENTION

The present invention relates to a patient monitoring system and more particularly to a vital signs monitor and an alarm system incorporated therein.

A need exists in the health care area for a low cost, reliable method of measuring patient respiration characteristics on a continuous basis and alarming when the measured parameters exceed certain preset thresholds.

Many situations exist where this monitoring capability can be life saving. Examples being (1) intraoperative monitoring in heavy sedation with or without local anesthesia (ultrasonic ovum retrieval, herniorrhaphy, breast biopsy, etc.), (2) emergency room monitoring, (3) recovery room monitoring, (4) intensive care unit monitoring, (5) patient transportation from an accident scene to a hospital, from a nursing home to the hospital, and finally during transportation of the patient after general anesthesia from the operating room to the recovery room.

The candidates for the monitoring are patients with or requiring (a) arrival in the recovery room after an operation which required heavy sedation with or without local anesthesia, (b) obstructive pulmonary disorders, (c) cardio vascular instabilities due to trauma, (d) post surgery anesthesia care, (e) high medicinal loading, (f) evaluation for commitment to ventilator support machines, (g) weaning from ventilators and (h) known predisposition to apnea episodes.

The monitor will alarm when threshold levels are exceeded relating to (1) tidal volume (TV) (volume of exhaled gas), (2) respiration rate (RR), (3) minute volume (RR×TV), (4) approximate oxygen consumed per breath, (5) approximate end tidal carbon dioxide, and (6) combinations of the above.

Additionally, the monitor will continuously display all analog values and the monitor will also provide a display of flow rate showing the dynamic movement of gases through the airway.

The monitoring of these vital signs is critical to the emergency and critical care patient. Changes in pulmonary function can signal life threatening events, respiratory arrest, apnea, hypoxemia and brain death.

Present technology relies on continual visual observation of a patient in a potentially threatening state, as well as an indirect measure of pulmonary or ventilatory function.

Visual observations have problems associated with it that are due to the inability of humans to provide continuous surveillance of a situation for a long period of time without loss of attention. This attention span is further minimized when duties are concurrently expanded to other tasks and patients.

Periodic blood gas analysis has value, but it is time consuming, and in acute changes of ventilation the time to act is very short. The blood gas analysis will show a trend in a patient's condition, but use of a mass spectrometer for the gas analysis has limited value especially in acute changes of ventilation and, thus, will not save a patient who experiences a rapid change in vital signs.

Continuous use of pulse oxyimeters will monitor arterial oxygen that is hemoglobin bound and provide readings of percentage saturation of hemoglobin (red blood cell) oxygen. This method has two major draw backs.

(1) When any patient motion exists at the sensor site the readings are unreliable due to the fact that the machine must necessarily look for readings that have noise artifacts and reject them when they are not compatible with prior averages. This causes present readings to be late. Since diminished pulmonary function can cause irreversible brain damage in 2 to 4 minutes, late readings are intolerable. Additionally, the patient at high risk frequently is being transported (motion) during the trauma, the trauma in and of itself can induce physical responses (motion).

(2) The rate that arterial oxygenation levels decline in the present of pulmonary arrest is dependant on several factors, namely, cardiac output, patient age, medicinal loading, physical condition, and other patient pathologies including poor peripheral perfusion. A common observation is complete pulmonary arrest, and oxygen arterial saturation levels of 80 to 95% several minutes after the pulmonary arrest.

Another method of assessing pulmonary function is to quantitize end tidal carbon dioxide. By measuring expired carbon dioxide as a percentage in terms of its partial pressure in the expired or exhaled gases, a measure of the rate of metabolism can be estimated since essentially all exhaled carbon dioxide which is the product of metabolism is excreted from the lungs through the mouth. Presently end tidal carbon dioxide is measured only in general anesthesia use. Even in the event that end tidal carbon dioxide was used universally, it is subject to problems associated with low tidal volume and the associated rebreathing of anatomical and mechanical dead space gases causing sufficient rises in the partial carbon dioxide pressures of exhaled gases. Also, at low respiration rates due to the solubility of carbon dioxide, it readily dissolves in blood gases by passing through tissue lining at very low partial pressures, allowing for false negative conditions to exist.

Further in an emergency environment false positives can occur as a result of esophageal carbon dioxide from stomach contents, for instance, beer and carbonated sodas.

A device is available that monitors the presence or absence of respiration by monitoring tidal flows and alarms at a preset time on the cessation of respiration. Such a device is disclosed in U.S. Pat. No. 5,063,938. The device disclosed in this patent does not provide quantitative information on patient tidal volumes.

SUMMARY OF THE INVENTION

An object of the present invention is to provide a vital signs monitor that obviates the above problems while at the same time provides a continuous monitoring capability that in addition to indicating quantitatively the tidal volume also is light weight, minimizes dead space, is self contained and low cost on a per procedure basis.

Another object of the present invention is to provide a vital signs monitor that allows the use of oxygen mask therapy as it is presently being used whereby the minute volumes of the incoming therapeutic oxygen substantially exceeds the patient's minute volume requirements, the excess passing through the monitor. This is fundamental to the invention in that the monitor does not alter this therapeutic procedure.

Still another object of the present invention is to provide a vital signs monitor for measuring tidal volumes accurately in the presence of excessive oxygen flowing through the mask in the non-intubated patient.

Two methods are provided for achieving this, namely:

(1) (a) measuring incoming oxygen temperature continuously, (b) measure exhaled temperature continuously, (c) compute continuously the percent of oxygen in exhaled flow from the knowledge that the incoming oxygen is lower in temperature than body temperature, and (d) compute tidal volume by integrating the expired flow rate of gas during exhalation. The expired tidal flow rate is the instantaneous total flow minus the instantaneous non inspired oxygen content. (2) (a) using the fact that the humidity content of the oxygen flowing through the mask is zero or known and that of the expired gas is 100%, calculate the percentage of oxygen in the total expired flow by measuring the absolute water content of the total expired flow continuously and from the reduction in humidity, compute the oxygen content continuously, and (b) subtract the percent oxygen from the total expired flow on a continuous basis and integrate for tidal volume through the entire exhale period.

Measurement of humidity uses an optical technique to measure the degree of absorption and scattering caused by the water vapor.

A further object of the present invention is to provide a vital signs monitor to measure end tidal carbon dioxide by an optical absorption method.

Still a further object of the present invention is to provide a vital signs monitor to measure heart rate by an optical method that measures the optical transmission through blood perfused tissue to detect the change in mass flow associated with the systolic and diastolic portions of the heart beat.

Another object of the present invention is to provide a vital signs monitor that enables the use of conventional oxygen therapy that has a formed mouth piece that is placed in the patient's mouth between the cheeks and gums with an airway that passes through the lips and additionally provides two channels for the nostrils allowing breathing to be oral, nasal or both.

Such a mask affords additional patient comfort while minimizing or eliminating leaks associated with conventional oxygen masks and at the same time substantially reduces dead spaces.

Still another object of the present invention is to provide a vital signs monitor with the ability to have alarm set points or threshold levels on all measured parameters.

These set points or threshold levels can be entered at the time of use by a clinician or automatically by a default mode program.

A further object of the present invention is to provide a vital signs monitor having the capability of being able to "play back" all measured values, in an historical fashion, through the instrument's displays or to a data logger.

Another object of the present invention is the provision of a vital signs monitor having an alarm processing capability that allows alarms to be generated from combinations of data conditions where the individual measurement values have not reached their individual set points or threshold levels, but when taken collectively according to other criteria an alarm condition exists.

A feature of the present invention is the provision of a vital signal monitor comprising first means adopted to be disposed at a selected location on a patient to pass at least exhaled gases therethrough; second means coupled to the first means to perform a plurality of resistive measurements of certain predetermined parameters of the exhaled gases and a plurality of optical absorption measurements of other predetermined parameters of the exhaled gases; and third means coupled to the second means responsive to the plurality of resistive measurements and the plurality of optical absorption measurements to provide individual read outs of at least a value of carbon dioxide in the exhaled gases, a value of tidal volume of the exhaled gases and a value of a respiration rate of the patient.

Another feature of the present invention is the provision of a fourth means in the above mentioned first means to measure changes or differences in mass flow of blood associated with systolic and diastolic portions of the patient's heartbeat, the fourth means being coupled to the third means to enable the third means to provide a read out of the heart rate of the patient.

A further feature of the present invention is the provision of a computer in the above mentioned third means to process the plurality of resistive measurements and the plurality of optical absorption measurements in accordance with a predetermined program to provide the read outs.

Still another feature of the present invention is the provision in the above-mentioned third means to provide first alarms when predetermined threshold levels of the values providing the read out are exceeded and a second alarm when the predetermined thresholds are not exceeded, but a combination of the values providing the read outs exceed other predetermined criteria.

BRIEF DESCRIPTION OF THE DRAWING

Above-mentioned and other features and objects of this invention will become more apparent by reference to the following description taken in conjunction with the accompanying drawing, in which:

FIG. 1A is an exploded perspective view of a simple version of the resistive measuring portion of the vital signs monitor in accordance with the principles of the present invention;

FIG. 1B is an enlarged view of the indicated portion of the resistive measuring portion of FIG. 1A.

FIG. 2 is a cross sectional view of the exhaled gas resistive measuring arrangement of FIG. 1;

FIG. 4A is a perspective view of a more sophisticated version of the disposable unit of the resistive measuring portion of the vital signs monitor in accordance with the principles of the present invention;

FIG. 4B is a view of a portion of the resistive measuring portion of FIG. 4A useful in explaining the operation thereof;

FIG. 5 is a cross sectional view of a simple version of the optical absorption measuring portion of the vital signs monitor useful in explaining optical absorption measurements to detect changes in the oxygen, humidity and carbon dioxide in exhaled gases in accordance with the principles of the present invention;

FIG. 6 is an exploded perspective view of a more sophisticated version of the disposable and reusable units of the optical absorption measuring portion of the vital signs monitor in accordance with the principles of the present invention;

FIG. 7 is an exploded perspective view of the vital signs monitor incorporating therein the resistive measuring portion of FIG. 4 and the optical absorption measuring portion of FIG. 6 in accordance with the principles of the present invention;

FIG. 9 is a perspective view of information input components and read out components of the vital signs monitor in accordance with the principles of the present invention;

FIG. 14A is a flow chart defining the operation of the computer of FIG. 13 in accordance with the principles of the present invention;

FIG. 14B is a curve useful in explaining the operation of the flow chart of FIG. 14A;

FIG. 15 is a schematic diagram of the electronic battery self checking circuit of FIG. 14 employed in the vital signs monitor in accordance with the principles of the present invention;

DESCRIPTION OF THE PREFERRED EMBODIMENTS

Figure 3B:
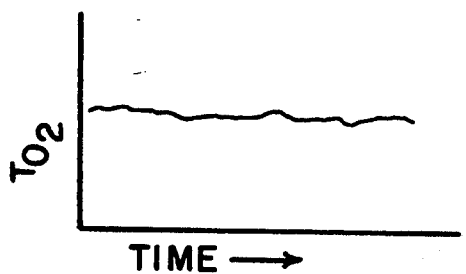
FIGS. 3A–3F are graphs useful in explaining the operation of the resistive measuring portion of the vital signs monitor in accordance with the principles of the present invention.

The envisioned range of application of the present invention is: (1) hospitals (a) transportation of patients, (b) operating room, (c) intensive care unit, (d) recovery room, (e) emergency room, (f) cardiac care and (g) pulmonary care; (2) nursing and home care—oxygen therapy for chronic obstructive pulmonary disease; and (3) emergency care, (a) first aid, (b) ambulance squads and (c) fire and police departments.

It is not the intent to restrict the application of the vital signs monitor of the present invention to the above, but to show the nature of its application within the health care community.

The description of the present invention evolves from the simple to the more sophisticated aspects of the instrumentation. It is understood that the more sophisticated instrumentation will consist of a combination of various measurement techniques combined in a single instrument providing the user with more measurements and greater precision using two techniques to measure the same parameter.

The simplest form of the device is oriented to measure (a) tidal volumes (TV), (b) minute volumes (MV) and (c) respiration rate (RR) for patients that have been intubated with an endotracheal tube and are not on a ventilation machine or anesthesia machine.

Such a patient may be supplied with supplementary oxygen, for instance, 5 to 10 l/m (liter per minute), through a "TEE" connection that mounts proximal to the flow sensor (in series with) which is plugged into the distal end of the endotracheal tube with a standard fitting.

The device measures tidal volume during exhalation. During exhalation the expired gases are at body temperature (37° C.) and at approximately 1 atmosphere of pressure. Additionally, the exhaled gases experience both high and low Reynolds numbers during a single exhalation causing the flow to be both turbulent and laminar.

The measurement is facilitated by the fact that 100% of the exhaled gas passes through the endotracheal tube, and due to the fact that the length to diameter ratio is substantially greater than ten, the flow profile will be radially symmetric about the axis of the tube, whether turbulent or laminar.

Taking advantage of the radial symmetry, a point flow measurement is made in the center of the exhaled stream of gases. The sensor, resistance means, is a heated element that is heated electrically, for instance, by a constant current source, above the temperature of the exhaled gases, for instance, 50° to 100° C., and has a resistance versus temperature characteristic that is sensitive to temperature changes. During the flow of gases over the sensor a cooling effect takes place due to the movement of the cool (37° C.) gases over the sensor. The flow causes the heated gas to be removed from the vicinity of the sensor and at the same time causes the temperature difference in the vicinity of the sensor to be greater, causing the sensor to lose heat more rapidly, thus changing its resistance. This effect is monotonic with flow rate.

If the sensor is supplied from a constant current source and its resistance decreases with increasing temperature, for instance, a thermistor, and its terminal voltage is the transduced parameter, a monotonic increasing relationship exists between flow and voltage.

To one skilled in the art the term "resistance means" used herein can be interpreted as any device having a temperature sensitivity and self heating ability, i.e. thermo couple, PN junction, wire resistivity vs. temperature, which is capable of performing a resistive measurement as described herein.

The above relationship is calibrated (linearized) by two nonlinear compensation networks. (1) The first network linearizes both the voltage vs. temperature characteristic, and the flow vs. temperature (local flow) characteristic. Since local flow and voltage are related deterministically only one network is necessary. (2) The mass flow through the endotracheal tube is related to its diameter (for a given flow rate) as is the critical Reynolds number (change in flow profile from parabolic to "blunt"). Since the measurement is a "center flow"

measurement, the second compensation network is required.

It should be noted that depending on the desired accuracy, tube-sizes, tidal volume and respiration rate, one compensation network could suffice. Also, if the sensor is placed at a venturi (narrowing) of constant diameter independent of tube diameter, the burden of the second compensation network is lessened at the expense of increased back pressure.

Referring to FIG. 1A, there is illustrated therein in an exploded perspective view a possible packaging configuration for the above mentioned resistive measuring device and the "bar graph" displays of the computer 1. Computer 1 has a bar display or read out 2 for the tidal volume, a bar graph display or read out 3 that dynamically displays the flow rate providing medical personnel with the rapid assessment aid and a bar graph display or read out 4 for the respiration rate.

An endotracheal tube 5 is attached to a housing 6 in which a sensor 7 is disposed. Housing 6 is a disposable plastic tube that mates with the endotracheal tube 5. As shown in the detail of FIG. 1B on the distal side of sensor 7 is a coned shaped baffle 8 which allows the exhaled gases to smoothly pass over sensor 7, while causing the inhaled gases to be blocked from sensor 7. This provides an asymmetry to the flow voltage which allows the ability to distinguish between inhalation and exhalation, and to determine the start of the exhalation to initiate the integration process.

It will be made clear in subsequent discussions that the electronics and displays can be miniaturized and be self contained within the sensor unit itself. This self contained miniaturized unit can be either disposable or have a removable electronics display package allowing that portion to be reusable.

In the post operative environment, emergency medicine care and with patients with pulmonary problems, face masks are frequently employed to provide therapeutic oxygen. In applying this oxygen therapy an amount of oxygen is provided to the patient at rates beyond his expected minute volumes, and the excess leaks out through vent holes, or through the face mask seal which is generally poor. The high flow rate of oxygen assures the patient an adequate supply of oxygen, while at the same time minimizing the amount of rebreathed air by "pushing" the residual amount of exhaled gases from the "dead space" of the mask.

While FIG. 1A discloses an outline of the operation and structure of the vital signs monitor in accordance with the principles of the present invention the following describes one particular instrumentation in greater detail. To one skilled in the art, alternative simple configurations or instrumentations will be obvious and it is the intent of this disclosure to protect all rights to the simpler obvious instrumentations.

Also different measurements are described and it is the intention of this disclosure to cover instruments that can be made from using single measurements, all the measurements within one instrument and all combinations of less than all the measurements.

The technology described will be implemented with several different specific techniques. For example, the signal processing could be implemented with (1) conventional analog circuitry employing either standard integrated circuit packages or surface mounted devices, (2) application specific integrated circuits whereby a custom chip would be fabricated to perform the necessary specific functions. It should be noted that the chip can be analog and do this specific processing in an analog fashion, digital whereby analog to digital converters digitize the signals and process them with binary logic under program control and a hybrid, a combination of the analog and digital approaches; and (3) computer techniques where a one chip computer or chip set computer, such as the Motorola 6805 series, whereby the necessary timers, CPU, RAM/ROM storage, clocks, stacks, I/O ports, display drivers etc. are available in an assembly language environment for implementing the routines.

The following detail description of the vital signs monitor in accordance with the principles of the present invention employs the computer implementation for ease of presentation, but is not intended to imply that it is the optimum implementation method. The optimum implementation is based on cost, performance criteria, size and weight.

Since one skilled in the electronics and computer arts can transpose one implementation into another, it is the intent to protect all such implementations.

Similarly, the display systems presented are but a few of the possible alternatives, but it is the intent to cover all obvious extensions of the basic concept.

FIG. 2 is a cross sectional view of a simple resistive measuring portion of the vital signs monitor of the present invention and FIGS. 3A–3F are graphs of some of the parameters present therein.

Referring the FIG. 2, there is illustrated in a cross-sectional view a disposable resistive measuring arrangement that can be employed as the resistive measuring portion of the vital signs monitor in accordance with the principles of the present invention. A main plastic housing 9 allows the unrestricted flow of oxygen therethrough. Housing 9 contains two valves 10 and 11. Both of valves 10 and 11 are one directional flap valves and are normally closed when no pressure difference exists. When the pressure on the left of each of valves 10 and 11 exceeds the pressure on the right they open. The inlet valve 10 allows the incoming flow of oxygen during inhalation. On exhalation from the lungs in passage way 12, the pressure in the chamber 13 between valves 10 and 11 will rise causing valve 10 to tend to close. With valve 10 closed, the exhaled gases will not go into the oxygen supply or the accumulator bag 14 thereby assuring that no expired gases will be rebreathed. While valve 10 is closed, oxygen is supplied into the oxygen accumulator bag 14 making a reserve of oxygen available for the next inhalation.

During exhalation, valve 11 is open due to the increased pressure created by the exhaled gases and possibly due to the flow of oxygen also. If the minute flow of oxygen is substantially greater than the patient's minute volume, the excess oxygen will pass through valve 11.

Housing 9 contains three temperature sensitive devices 15, 16 and 17. Temperature sensitive device 15 measures the incoming temperature of oxygen ($T_{o2}$), temperature sensitive device 16 measures the temperature of the combination of the exhaled gases and oxygen ($T_{EX}$) and temperature sensitive device 17 measures ambient temperature ($T_A$) and flow ($F_v$) through the venturi tube 18. Temperature sensitive sensor 17 is self heated as previously described to well above the maximum expected ambient temperature (50°–100° C.).

The values $F_V$, $T_{o2}$, $T_{EX}$ are continuously monitored, for instance, sampled at a rate substantially higher than the respiration rate (50 to 200 times higher).

Figure 3A:
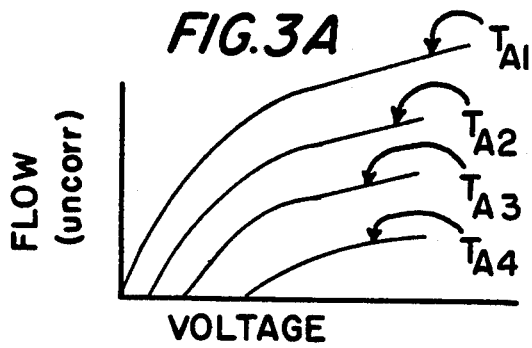

$T_A$ is sampled once per breath and will have the characteristics as shown in FIG. 3A.

$T_{o2}$, the temperature of the incoming oxygen, is relatively constant and cool as shown in FIG. 3B. The resistance value of the sensor measured with a bridge or a very low known current is applied momentarily (to avoid self heating) and a voltage is read and the resistance is calculated. With this calculated value of resistance, a look up table (LUT) is entered and an absolute temperature is stored.

Figure 3C:
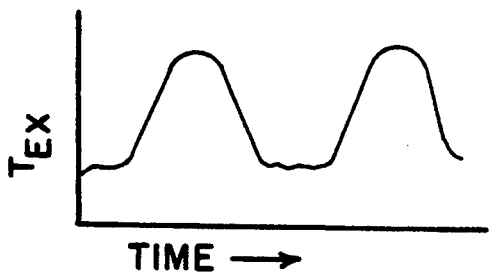
Figure 3D:
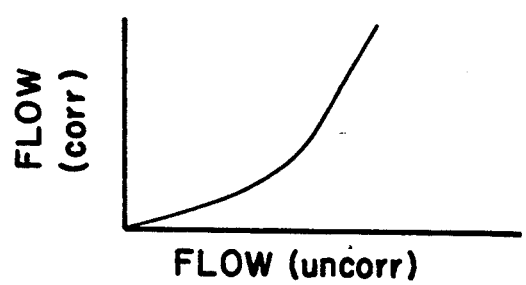

$T_{EX}$ is measured in the same fashion, converted and also stored in the computer. Due to the respiration, this temperature changes with respiration rate as shown in FIG. 3C, and the sampling rate is sufficiently high to follow the changes. For high respiration rates, $d\Delta T_{EX}/dt$ may cause the sensor response time to interfere with the accuracy. This can be compensated for by measuring $dT_{EX}/dt$ and compensating $T_{EX}$ from look up tables. This is illustrated in FIG. 3D.

Figure 3E:
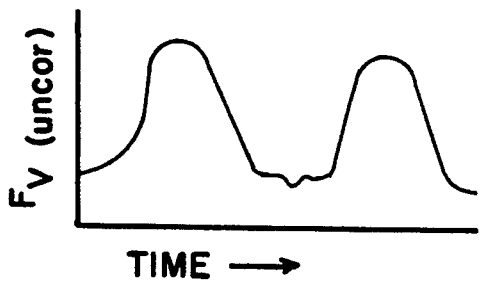

The flow $F_V$ in the venturi tube 18 is monotonically related to the flow in the main housing 9 to the right of valve 11. This is illustrated in FIG. 3E.

As the mixture moves to the right, a low pressure region is formed where the venturi 18 meets the housing 9, causing ambient air to be drawn through the venturi 18.

The reason for generating the side stream flow is two fold: (1) is keeps the flow sensor 17 out of the main stream of exhaled gases where moisture could interfere with the response time, and (2) the main stream flow is efficiently lengthened by the sinusoidal variations in its direction. This has the effect, in addition to adding length, of adding a slight resistance or back pressure (1–10 mm of water) causing the flow near venturi 18 to be repeatable across its cross section (rectangular in to the page) independent of particular patient anatomy or respiration differences which occur to the left of valve 11.

The flow transducer only measures flow at a point, and by placing it in a side stream of flow, the venturi 18 can be smoothly necked down to a circular cross section where the mass flow is predictable. Further, where it meets the main stream flow, the venturi 18 effectively samples across the entire width, not missing any of the main stream flow.

Figure 3F:
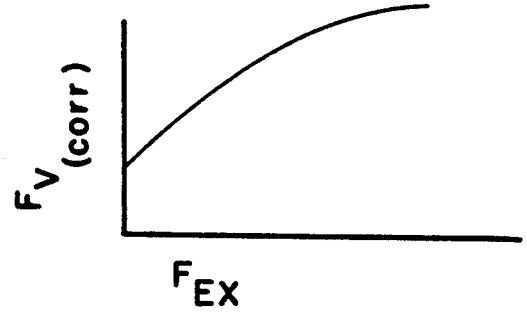

The flow $F_V$ as a function of time is shown in FIG. 3E (the raw uncorrelated flow) as peaking during exhalation and essentially no flow during inhalation. Since the sensor 17 is temperature sensitive it needs to be corrected for the ambient temperature. FIG. 3A depicts a family of voltage vs. flow curves for differing ambient temperatures. When the sensor 17 is supplied with a constant current it will have a certain voltage across it with no flow that is related to the temperature. Therefore, by sampling the voltage at no flow (inhale) and using a LUT, the ambient temperature can be determined along with the flow characteristics for that ambient temperature. During exhalation there are two non-linearities that have to be corrected (combined into one LUT) (1) the actual flow in the venturi 18 vs. the measured flow as shown in FIG. 3B, for instance, turbulence effects, the transition to laminar and cross sectional area at sensor 17, and (2) the non linearity associated with the main stream flow $F_{EX}$ and the actual venturi flow as illustrated in FIG. 3F.

Once these corrections are made $F_{EX}$ is known. $F_{EX}$ is the total flow rate out of housing 9 and it consists of the exhaled gases plus the unbreathed oxygen flowing through the system.

The object is to determine the percentage of unbreathed oxygen flow through the system with the exhaled gases on an instantaneous basis.

If $P_{o2}(t)$ = instantaneous % of unbreathed $O_2$ and $F_{EX}(t)$ = total flow rate from housing 9 then the tidal volume TV becomes $$TV = \int_{\substack{\text{breath} \\ \text{period}}} [1 - P_{o2}(t)] F_{EX}(t) dt$$

Both terms remain inside the integral because they are time dependent.

In a computer based system both $F_{EX}(t)$ and $P_{o2}(t)$ would be sampled quantities and for constant sampling intervals;

$$TV = \sum_{\substack{\text{breath} \\ \text{period}}} [1 - P_{o2}(t)] F_{EX}(t) dt$$

The sum can be over the entire breath period because during inhale $P_{o2}(t)$ approaches 100%, and does not contribute to TV.

Since the inhale volume does not necessarily equal the exhaled volume from a mass flow view point due to the fact that oxygen is inhaled at one temperature and part of it exhaled at another temperature and the exhaled gases contain oxygen, carbon dioxide, and water all at a different temperature from the inhaled oxygen.

The objective of finding the $P_{o2}(t)$ can be accomplished by noting that if the process is considered essentially isobaric (1 atmosphere) and the thermal losses after exhalation are minimal, the gases can be considered as two streams blending together, one stream being the unbreathed oxygen $T_{o2}$, the other stream the exhaled gases oxygen, carbon dioxide and water at $T_{EX}$.

By way of analogy consider the mass of gases that would flow per unit time with the following designations:

$T_1$ = Temp. unbreathed $O_2$
$T_2$ = Temp. exhaled gases (37° C.)
$T_3$ = Temp. of Mixture
$m_1$ = Mass unbreathed $O_2$
$m_2$ = Mass Exhaled $O_2$
$m_3$ = Mass Exhaled $CO_2$
$m_4$ = Mass Exhaled $H_2O$
$P_1$ = Partial Pressure $O_2$ Unbreathed
$P_2$ = Partial Pressure $O_2$
$P_3$ = Partial Pressure $CO_2$ Exhaled
$P_4$ = Partial Pressure $H_2O$ (As a %)
$M_{1,2}$ = Molecular Weight $O_2$
$M_3$ = Molecular Weight $CO_2$
$M_4$ = Molecular Weight $H_2O$
$C_{V1\&2}$ = Thermal Capacity (Spec. heat) $O_2$
$C_{V3}$ = Thermal Capacity (Spec. heat) $CO_2$ Const
$C_{V4}$ = Thermal Capacity (Spec. heat) $H_2O$ Vol.
$F_{EX}$ = Total Flow of Gases R = Universal Gas Constant = 1.987 cal/gm (calorie per gram)
$n_1$ = # of molecules/sec $O_2$ incoming
$n_2$ = # of molecules/sec $O_2$ exhaled
$n_3$ = # of molecules/sec $CO_2$ exhaled
$n_4$ = # of molecules/sec $H_2O$ exhaled Considering the two streams of unbreathed oxygen and exhaled gases before mixing and, since there is no chemical reaction, the thermal energy in one second of flow is the sum of the thermal energies from each stream, for instance, $$[m_1 C_{v1}] T_1 + \left[ \sum_{i=2}^{4} m_i C_{vi} \right] T_2$$

After those two portions of gas are mixed the energy must be the same ± mechanical work done to maintain constant pressure;

$$= \left[ \sum_{i=1}^{4} m_i C_{vi} \right] T_3 \pm [\text{WORK DONE}]$$

The work performed by the unbreathed oxygen results from its increase in temperature causing it to expand in order to maintain constant pressure. The heat loss associated with this expansion is;

$$- \frac{m_1}{M_1} R(T_3 - T_1), \frac{m_1}{M_1} = \text{\# of molecules/sec}$$

The work done on the exhaled gases is from their cooling upon mixing, resulting in an increased density, adding energy to the mixture. For instance, $$+ \left[ R \sum_{i=2}^{4} \frac{m_i}{M_i} \right] (T_2 - T_3)$$

The total energy balance relationship is then;

$$[m_1 C_{v1}] T_1 + \left[ \sum_{i=2}^{4} m_i C_{vi} \right] T_2 = \left[ \sum_{i=1}^{4} m_i C_{vi} \right] T_3 -$$

$$\frac{m_1}{M_1} R(T_3 - T_1) + R \left[ \sum_{i=2}^{4} \frac{m_i}{M_i} \right] (T_2 - T_3)$$

REWRITING:

$$\left[ \sum_{i=2}^{4} m_i C_{vi} \right] (T_2 - T_3) = m_1 C_{v1} (T_3 - T_1) -$$

$$\frac{m_i}{M_1} R(T_3 - T_1) + \left[ R \sum_{i=2}^{4} \frac{m_i}{M_i} \right] (T_2 - T_3) \left\{ \left[ \sum_{i=2}^{4} m_i C_{vi} \right] - R \left[ \sum_{i=2}^{4} \frac{m_i}{M_i} \right] \right\} (T_2 - T_3) = \left[ m_1 C_{v1} - \frac{m_1}{M_1} R \right] (T_3 - T_1)$$

converting mass/sec. to molecules/sec.

$$\left[ \sum_{i=2}^{4} n_1 M_i C_{vi} - R \sum_{i=2}^{4} n_i \right] (T_2 - T_3) =$$

$$[n_1 M_1 C_{v1} - n_1 R](T_3 - T_1)$$

Since the ratio of partial pressures in the exhaled gas to the atmospheric pressure are equal to the ratio of the number of molecules to the total number of exhaled molecules independent of the type of gas.

$$\frac{p_2}{p_A} = \frac{n_i}{n_t}, \frac{p_3}{p_A} = \frac{n_3}{n_t}, \frac{p_4}{p_A} = \frac{n_4}{n_t}$$

Where:
$p_A$ = Atmospheric Pressure $n_t$ = total molecules/sec exhaled
$\phantom{n_t}$ = $n_2 + n_3 + n_4$ And $$n_i = \frac{n_t}{p_A} p_i$$

Substituting;

$$n_t \left[ \sum_{i=2}^{4} \frac{p_i}{p_A} M_i C_{vi} - R \right] (T_2 - T_3) =$$

$$n_1 [M_1 C_{v1} - R](T_3 - T_1)$$

OR $$\frac{n_1}{n_t} = \frac{\left[ \sum_{i=2}^{4} \frac{p_i}{p_A} (M_i C_{vi}) - R \right]}{[M_1 C_{v1} - R]} \cdot \frac{(T_2 - T_3)}{(T_3 - T_1)} = r_n$$

Where $n_1/n_t$ is the ratio of exhaled molecules to unbreathed oxygen molecules:
The ratio of the masses being;

$$r_m = r_n \left[ M_1 / \sum_{2}^{4} \left( \frac{p_i}{p_A} \right) (M_i) \right]$$

$$m_1 = n_1 M_1$$

$$m_t = n_2 M_2 + n_3 M_3 + n_4 M_4$$

$$\phantom{m_t} = \frac{n_t}{p_A} \left[ \sum_{2}^{4} p_i M_1 \right]$$

$$\frac{n_1}{n_t} = r_n$$

$$r_m = \left\{ \frac{M_1}{\sum_{i=2}^{4} \frac{(p_i M_i)}{p_A}} \cdot \frac{\left( \sum_{i=2}^{4} [(p_i/p_a) M_i C_{vi}] - R \right)}{(M_1 C_{v1} - R)} \right\} \frac{(T_2 - T_3)}{(T_3 - T_1)}$$

The relationship for $r_m$ involves the two measured temperatures $T_1$ and $T_3$ plus the atmospheric ratios of alveolar partial pressures to atmospheric pressures.

The variation in $r_m$ as a function of altitude is minimized due to the fact that at higher altitudes the partial pressures required for alveolar capillary exchanges lapse with altitude except for the saturated vapor pressure of water which in terms of expirational gases tends to be constant with altitude.

A precise instrument could be fabricated considering above and compensating with atmospheric pressure and although this instrument is part of this disclosure, it is not part of the embodiment being presented here. $r_m$ for embodiment presented herein is;

$$r_m = \zeta(T_1, T_3) = K \left[ \frac{T_2 - T_3}{T_3 - T_1} \right]$$

The instantaneous percentage of non breathed oxygen in the output flow is;

$$P_{o2}(t) = \frac{m_{o2}}{m_{o2} + m_{EX}} = \frac{1}{1 + m_{EX}/m_{o2}} = \frac{1}{1 + 1/r_m}$$

and $$1 - P_{o2}(t) = \frac{1}{1 + r_m}$$

Tidal Volume becoming $$TV = \sum_{\substack{\text{Breath} \\ \text{Period}}} \left( \frac{F_{EX}}{1 + K\left(\frac{T_2 - T_3}{T_3 - T_1}\right)} \right) \Delta t$$

Noting that if all the oxygen is inspired ($T_2=T_3$), the TV is the integrated value of $F_{EX}$, and if none is inspired ($T_1=T_3$) the integrated tidal volume is O.

Clearly, since the percentage of unbreathed oxygen is known, and the body temperature is known, the partial pressure of water is known. Therefore, if exhaled carbon dioxide is estimated (i.e. 5% or 40 mmHg) or measured as discussed later an estimate of the oxygen consumed can be made.

Clearly, if a known percent of nitrogen was mixed with the oxygen and assuming the body was nitrogen balanced (inspired mass equals expired mass) the above analysis would only have to be augmented with the atomic weights an specific heats of nitrogen and the results would be the same. Similarly, if dry atmospheric air was considered and assumed to have its normal mixtures of gases the analysis would provide the same results.

Similarly, if moist water vapor was mixed with dry atmospheric air and a measurement of the precipitable water was made, as will be described hereinafter, over a fixed path length, again the tidal volume (TV) could be calculated with the above technique. Fully saturated air at 25° C. is only 25 mmHg and could be neglected.

Since the tidal volume (TV) contains a known amount of water plus carbon dioxide, the TV minus the volume of carbon dioxide and water is the amount of exhaled oxygen (or oxygen plus nitrogen if a mixture was supplied).

The inhaled oxygen is the total amount of oxygen ($O_{2T}$) provided in time T minus $$\int_\tau P_{o2}(t) dt \quad \tau = \text{several breath periods}$$

$$O_{2T} - \int_\tau P_{o2}(t) dt = O_{2IT} \text{ (INHALED) in } \tau$$

$$\int_\tau TV(t) - \int_\tau [H_2O(t) + CO_2(t)] dt =$$

$$O_{2ET} \text{ (EXHALED) IN } \tau$$

$$\therefore O_{2AT} \text{ (Absorbed in } T \text{ sec's)} = O_{2IT} - O_{2ET}$$

Since water is known from its partial pressure and carbon dioxide is measured optically, (mass flow) $O_{2AT}$ can be readily calculated by the addition of a flow sensor (identical to $F_v$) in the oxygen line.

After several seconds of accumulating data, $O_{2AT}$ per breath can be calculated and related to tidal volume. Several breaths being required since the oxygen does not necessarily follow the respiration cycle.

The following paragraphs describe more sophisticated equipment used for making the resistive measurements described in the above analysis. To one skilled in the art modifications to accommodate the additional measurements described would not require additional inventions.

Figure 8:
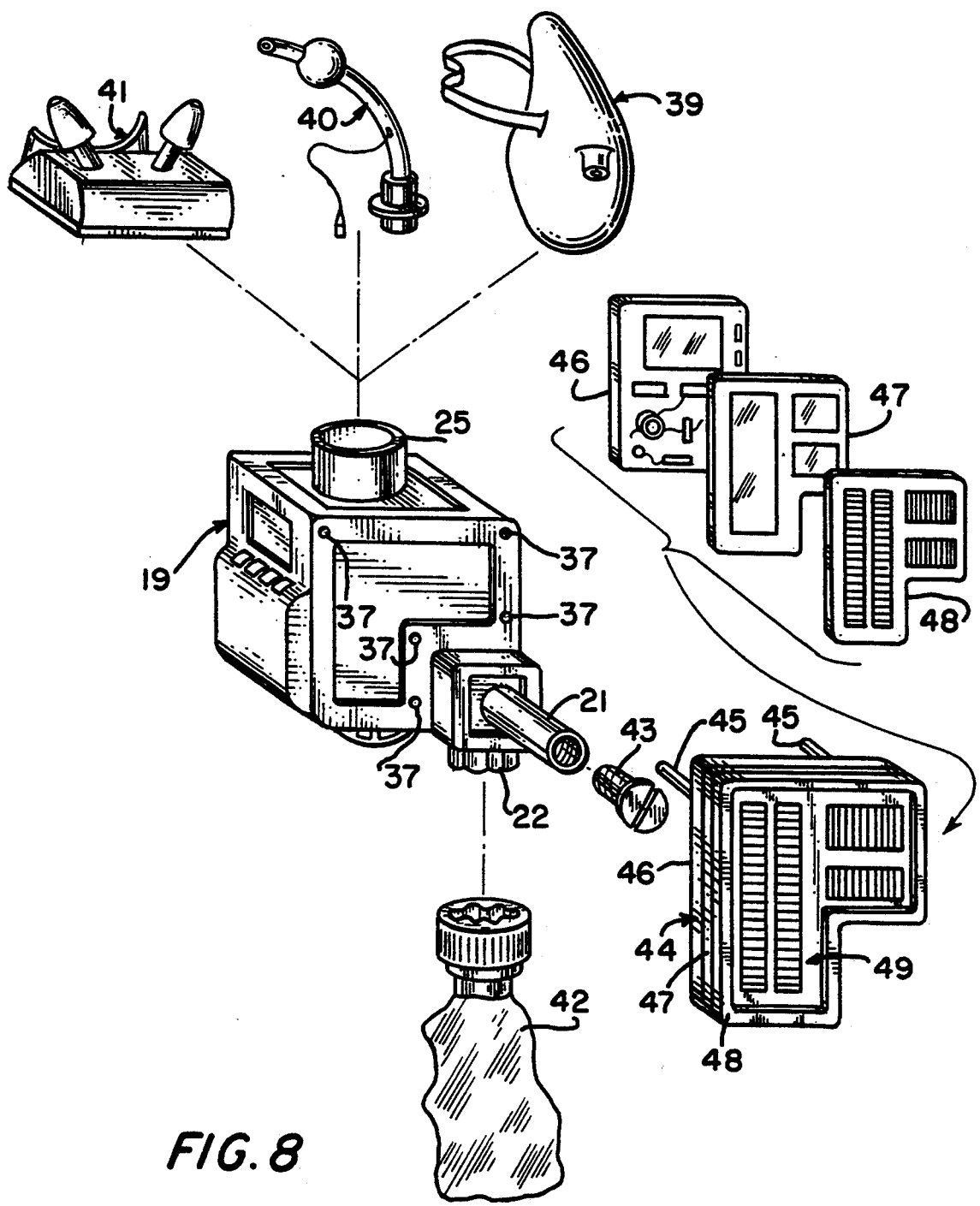
FIG. 8 is an exploded perspective view illustrating certain of the components of the vital signs monitor in accordance with the principles of the present invention.

Referring to FIGS. 4A and 7 there is illustrated in perspective view a disposable component which would be common to all possible physical configurations of the overall equipment in accordance with the principles of the present invention. A molded plastic housing 19 contains several distinct chambers to facilitate the above described resistive measurements. Housing 19 contains batteries 20 in compartments molded into housing 19 that provides operating power to the plug-in processor unit as shown in FIGS. 7 and 8.

Oxygen is supplied to fitting 21 where it can pass into a reservoir bag 42 mounted to the standard fitting 22 and/or pass through flap valve 23. Resistive temperature sensor 24 measures the oxygen temperature continuously. Upon inhalation, valve 23 opens allowing the unrestricted flow of oxygen to enter and pass out through the standard fitting 25 providing oxygen to the patient. During inhalation, flap valve 26 closes due to the pressure in the upper chamber 27 falling below atmospheric.

Upon exhalation, the pressure in upper chamber 27 is above atmospheric pressure causing valve 26 to open and valve 23 to tend to close.

The exhaled gases and unbreathed or noninhaled oxygen passes through valve 26 and mix rapidly and exchange energy as they enter the corrugated chamber 28 as indicated by a temperature change detected by temperature sensitive resistive device 29. Chamber 28 causes a slight back pressure causing a more uniform distribution of pressure and minimizing irregular flows. As the gases approach the bottom of chamber 28 they reach a lip 30 that passes to the exhaust area 31. As the gases pass over lip 30, a low pressure region is created across the full length of lip 30 causing ambient air to move through inlets 32 and flow through a calibrated venturi chamber 33 where the flow of this air is measured by resistive sensor 34. In FIG. 4B, curve 35 shows the air flow pattern for the ambient air through venturi 33 and curve 36 illustrates the flow of the gases in corrugated chamber 28.

Several connections 37 are provided for providing electrical connections as well as a mounting method for securing the disposable element to the reusable processor shown in FIGS. 6, 7 and 8. A connector 38 is provided for connecting a heart rate monitor to the electronics contained in the processor, such as computer 1 of FIG. 1 and circuit boards 46, 47 and 48 of FIGS. 6, 7 and 8.

An additional method of determining the percentage of oxygen that was unbreathed during respiration but passed through the mask is found by considering the partial pressure shift in water as a vapor or gas.

Only a brief description is given since once the fractional part of unbreathed gas is determined, the subsequent analysis is obvious in light of the forgoing.

Further, the following describes a method of determining $P_{O2}(t)$ in the presence of pure oxygen and nitrogen as a dry gas. But it is clear, if desired, that the same technique used for measuring water in the exit gas stream could be employed to measure water in the source gas stream allowing the system to deal with the breathing of moist atmospheric air.

The exhaled gases are 100% saturated (humidity) with water vapor independent of the inhaled gas mixture, and independent of pressure. Saturated vapor pressure is exclusively a function of temperature, i.e. 37° C. 47 mmHg.

The density of the saturated water vapor is $$\rho_{sv} = m_w/V_v \quad \begin{array}{l} m_w = \text{Mass} \\ V_v = \text{Volume of Vapor} \end{array}$$

the density of water precipitated out of the vapor (water)

$$\rho_w = m_w/V_w = 1 \text{ Gm/cu cm} \quad V_w = \frac{m_w}{\rho_w} = \rho_{sv} V_v$$

$V_w$ = Volume of Water

If a tube of radius R and length L was filled with a water saturated gas the volume would be;

$$V_v = \pi R^2 L$$

If the water was then precipitated out of the gas into cylinder of the same radius its mass would be;

$$m_w = \rho_{vs} \pi R^2 L$$

and its volume would be
$v_w = m_w$ since 1 cc=1 gm and the height would be $$\frac{v_w}{\pi R^2} = \rho_{vs} L$$

For example at 35° C. the density of saturated water vapor $$\frac{39.19}{1 \times 10^6} \text{ g/cu cm}$$

Over a path length of two inches the precipitable water is in mm;

$$l_{wmm} = \frac{39.19}{1 \times 10^6} \cdot 10 \cdot 2.54 \cdot 2 = .002$$

If an optical frequency $\lambda$ is selected where there is a tendency to absorb the optical energy $A(\lambda)$, and scatter the optical energy $E(\lambda)$ from its path, an optical receiver at the end of the path will measure the amount of light that is received after scattering and absorption.

Considering a distance L through the atmosphere, the ratio of power transmitted ($P_O$) to that received (P) is $T(\lambda)$ and $$T(\lambda) = \frac{P}{P_o} = e^{-[A(\lambda)+E(\lambda)]L}$$

extinction factor $\alpha(\lambda)=[A(\lambda)+E(\lambda)]T(\lambda)=e^{-\alpha(\lambda)L}$
expressed in terms of precipitated water; $T(\lambda)=e^{-\alpha(\lambda)\rho(1w/vs)}$ Tables exist in the book Larmore and Passman, "Atmospheric Transmission", The Rand Corporation, July 1956, for the determination of transmission through precipitable water i.e. at $l_w = .1$ mm $T(\lambda) = .138$ for; $\lambda = 6.6\mu$ inferring; $\alpha(\lambda) = \frac{\ln(T(\lambda))}{-l_w} = \frac{\ln(.138)}{-(.1)} = 19.81$ therefore for; $\lambda = 6.6\mu$
$T = 35°$
$L = 2''$ the $l_w = .002$
$T(\lambda) = e^{(19.81)(.002)} = .9612$ Since $l_w$ is proportional to the relative humidity, if a volume of gas is added (mixed) with the saturated gas and the pressure remains constant (atmospheric), the number of water molecules per unit path length as proportionally reduced.

$$-\alpha(\lambda)l_w = \frac{(100)}{100 + P(O_2)}$$

i.e. $T(\lambda) = e$

If the mixture was $P(O_2) = 10\%$ then: $T(\lambda) = e^{-(19.81)(.002)\frac{(1)}{1.1}}$
10% $\qquad = .96518$ If it was 100%

$T(\lambda) = e^{-(19.81)(.002)/2}$
100% $\qquad = .981$

Giving a method of measuring P ($O_2$).

The use of $\lambda=6.6\mu$ is by way of example only since several absorption windows for water exist in the atmosphere.

A similar measurement technique can be used for measuring carbon dioxide on a continuous basis, which has value to the invention in that it provides a very direct measurement of metabolic state, or the alveolar capillary exchange of oxygen and carbon dioxide. The measurement of carbon dioxide also provides a basis for calculating cardiac output which the vital signs monitor of the present invention will provide. For instance, Fick cardiac output, "Clinical Application of Blood Gases", Barkley A. Shapiro Appendix 1-A, Page 157, Year Book Medical Publishers, Inc., 1973 Chicago LCCCN 72-93720.

Since normal atmosphere contains approximately 0.00033 carbon dioxide, the exhaled carbon dioxide represents the exchanged gas, and is therefore a measure of homeostasis.

From the preceding referenced tables in the book authored by Larmore and Passman, it can be found that for a path length of 100 m at an optical frequency of 4.3μ the atmospheric transmission is 0.098.

The path length infers the number of absorbing molecules encountered at normal atmospheric conditions. The number of molecules encountered at other than atmospheric conditions can be related to the partial pressure and an effective path length.

$$T(\lambda) = e^{-\alpha P_{CO_2} l}$$

$$\alpha = \frac{\ln(T(\lambda))}{P_{CO_2} l}$$

for the conditions given where;

$$P_{CO_2 Atmos} = (.00033)(760) = .25 \text{ mm Hg}$$

$$l = 100 \text{ m} = 3.937 \times 10^3 \text{ inches}$$

$$\alpha = \frac{\ln(.098)}{-(.25)(3.937 \times 10^3)} = .00236$$

Therefore, for a normal human $P_{CO_2} = 40$ mmHg, measured over 2", the transmission should be $$T(\lambda) = e^{-(0.00236)(40)X2} = 0.827$$

a readily detectable value.

In order to implement the carbon dioxide and water measurements in the instrument of the present invention, light filters, light sources and photosensors are required.

The light source can be broad band centered (if possible) on the selected frequency. If its spectrum can be considered uniform and a band width $BW_{LS}$ with a total power output of $\Phi_{LS}$ in the direction of the photo sensor, its power per cycle of band width is; $\Phi LS/BW_{LS}$ The light filter must be of sufficiently narrow band width to be able to select the desired frequency band width, $(BW)_f$ (i.e., 0.05μ). This filter can be fabricated from combinations of high pass and low pass filters using thin film deposited layers to achieve the desired results employing interference techniques.

The photo sensor must have the ability to convert incoming photons at the desired frequency to electrons (ξ = # of electrons/photon) and in the case of a phototransistor multiply them by a gain factor (i.e. $\beta = \partial IC/\partial IB$). If a collector resistor (R) is used to develop a voltage, i.e. with respect to ground on a PNP phototransistor, this voltage would be (neglecting biasing)

$$V_o = \xi' \frac{\Phi}{(BW)_{LS}} (BW)_f \beta R e^{-\alpha PL}$$

OR

-continued $$\frac{\Delta V_o}{V_o} = -\alpha L \Delta P \quad \begin{array}{l} L = \text{path length} \\ P = \text{partial pressure} \end{array}$$

The above description applies to both carbon dioxide and water or any other gas where the absorption frequencies do not interact, i.e., absorption of carbon dioxide does not effect water monitoring.

Absorption techniques have been used for many years and generally requires calibration. The uniqueness of the proposed method is that it is self calibrating and alternating current coupled.

By supplying a continuous source of gas, not containing the gases to be detected, in quantities sufficiently small to just clear (empty) the optical chamber 65 of FIG. 5 of the previously measured gases, during inhalation (i.e., valve 26 of FIG. 4A closed), a reference point of "O" absorption can be established. This process will repeat every breath cycle.

The continuous flow of oxygen will not influence the reading of tidal volume, carbon dioxide or water in that the basic measurements consider a certain amount of oxygen at $P_{O_2}(t)$.

Therefore, the instantaneous partial pressures will be referenced to the "non absorption" base line and integrated through the exhalation cycle to determine end tidal volume, carbon dioxide and/or percent of water. The band width of the amplifier has to be low enough to pass the repetition rate undistorted (i.e., 2 cycles per minute).

FIG. 5 is a cross sectional view and FIGS. 6 and 7 are perspective views illustrating the optical absorption measuring portion of the vital signs monitor of the present invention including the above discussed chamber. Two sets of optical absorption gas detectors are shown. The first detector includes a light source 66 providing the band width required, a filter window 67, a reflector 68 having a high reflectivity at the sampling frequency (λ) and a photosensor 69. The second detector includes a light source 70 providing the band width required, a filter window 71, a reflector 72 having high reflectivity at the sampling frequency (λ) and a photosensor 73. The first detector could be a humidity detector while the second detector could be the carbon dioxide detector. It is to be understood that the roles of the first and second detectors could be reversed. The light sources and photosensors are provided on circuit board 46 as shown in FIGS. 6 and 7. Also the filter windows could be provided in a circuit board 46a as shown in FIG. 7 so that the circuit board package including boards 46 and 46a are reusable. In this arrangement the filter windows would not be discarded with disposable unit 19 thereby reducing the cost of disposable unit 19.

FIGS. 6 and 7 illustrates the situation in three dimensions showing the passage of the light beam through approximately twice the cavity height.

The surface of the exhalation or corrugated chamber 28 can be lined with a moisture absorbing layer and/or apertures in the surface to allow the flow of condensed moisture to leave chamber 28.

Further the possibility of slight condensation exists on the optical surfaces and if necessary they will be heated (i.e., 40° C.). Due to their minimal area, heating requirements are small and could be provided by a partially conducting layer over the filters and reflectors with a optically non absorbent material. Chemical surface wetting could aid in overcoming the problem.

FIG. 8 illustrates how the instrumentation of FIG. 7 of the vital signs monitor is utilized in accordance with the principles of the present invention. The interface to the patient can be a conventional oxygen therapy mask 39, an endotracheal tube 40 or a nasal-oral ventilation adaptor 41. Each of the interface devices have a standard fitting allowing it to be readily mounted to the disposable element 19 of FIG. 7. Disposable element 19 can be used with standard reservoir bags 42 mounted with standard fittings, or it can be used without bag for breathing ambient air and plugging the oxygen supply line 21 with a plug 43.

The processor/display unit 44 mounts via electrical connectors 45 to the connectors 37 of disposable unit 19.

The processor/display unit 44 consists of three principle layers. The electronic layer 46 provides the substrate, wiring, electronics and optical components connected to the disposable unit 19 as well as a serial data port connector to programmer and changer unit. The alarm and low power battery circuitry are also located on this layer. Layer 47 is a lower power electroluminescent display screen that provides back lighting for the front surface LCD (liquid crystal diodes) display. The surface areas that are illuminated are only those areas that fall below the active liquid crystals in order to save power. The layer 48 is the LCD display which is controlled by the processor and provides real time displays of the measured parameters, alarm set points and historical data. Depending on the application, the display can be bar graphs as shown at 49 of FIG. 5, or a digital display as shown in FIG. 9 at 50. FIG. 7 illustrates the complete disposable unit 19 and its associated circuit boards to enable measuring all of the vital signs defined by all of the above equations.

FIG. 9 illustrates an alternative design configuration for the processing unit and read out unit 51. The design configuration that provides a historical hard copy record 52 of all parameters and mounts on an equipment pole 53 by the patient or is attached to the bed.

A hand held or wall mounted programmer/reader unit 54 can be provided that allows the alarm set points or threshold levels to be entered into the processor/display unit 44 of FIG. 8 or 50 of FIG. 9 for display thereof and also to allow historical data to be read back to the user 55 providing a minute by minute history of the data points.

As pointed out above an object of the present invention is to be able to concurrently process alarms for the vital signs monitor in accordance with the principles of the present invention as well as other sensors that are electrically connected to the unit 51. Historical patient data can also be entered into the device (size, age, pathologies, medicinal loading, etc.) via a computer 56 which also enters a hyperdimensional alarm surface into the unit that permits the unit to alarm on a single value alarm or combination of variables each of which are below their respective alarm point or threshold, that indicate a threatening situation.

Figure 12:
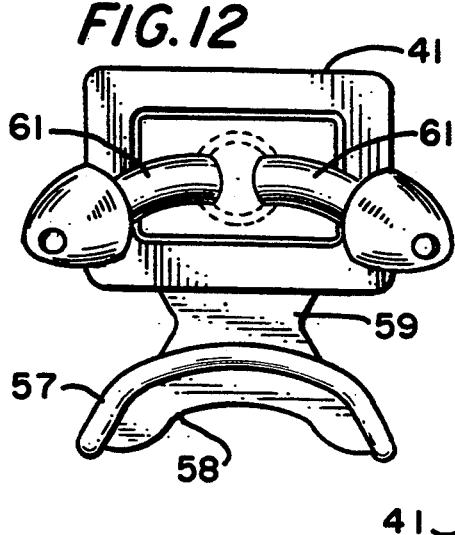
FIG. 12 is a top view of the nasal-oral ventilation adaptor of FIG. 10.
Figure 11:
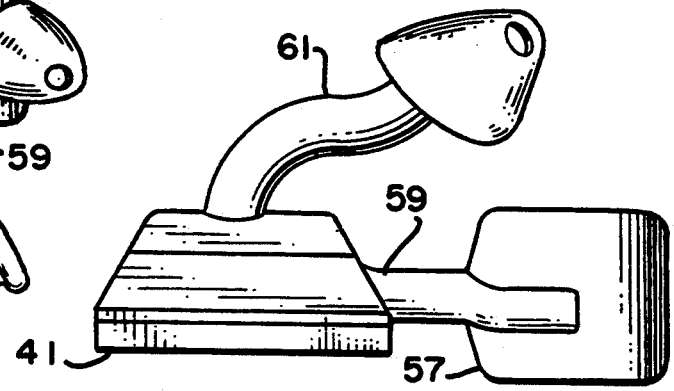
FIG. 11 is a side view of the nasal-oral ventilation adaptor of FIG. 10.
Figure 10:
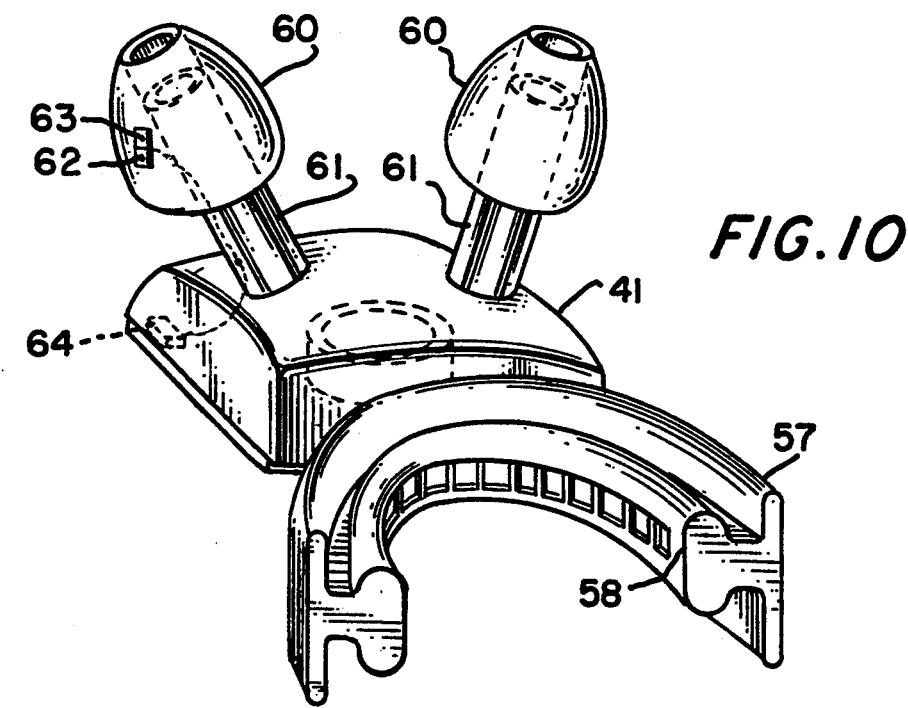
FIG. 10 is a perspective view of one embodiment of the nasal-oral ventilation adapter employed in the vital signs monitor in accordance with the principles of the present invention.

FIGS. 10, 11 and 12 illustrate the nasal-oral ventilation adaptor 41 of FIG. 8 in several views. Adaptor 41 is molded in a soft durable plastic in several sizes to accommodate anatomical differences.

The outer rim 57 of the mouth piece will fit between the gums or teeth and the cheek of the patient. The inner rim 58 will provide a biting surface and serve as the oral portion of the air way. The air will pass through the wide channel 59. Additionally, nasal passage ways will be provided by tubular structures 60 to enable insertion in the patient's nostrils that are sufficiently flexible to bend and accommodate different facial structures. Adjustable nostril inserts 60 made of soft pliable plastic extend from tube 61 and provide a seal at the patient's nose.

The patient normally can breath through both the nose and mouth although providing plugs in the appropriate passages breathing can be directed through either nostril or through the mouth.

A light emitting diode 62 and a photo sensor 63 are provided in one of the nostril inserts 60 that are controlled in optical frequency to reflect off the perfusing blood in the nostril. The photo sensor 63 and the light source 62 look for the systolic and diastolic changes or differences in reflection during a heart beat to measure the heart rate.

Power and signals are communicated through a three terminal connector 64. The output signal from connector 64 is supplied to the processor/display unit 44.

Figure 13:
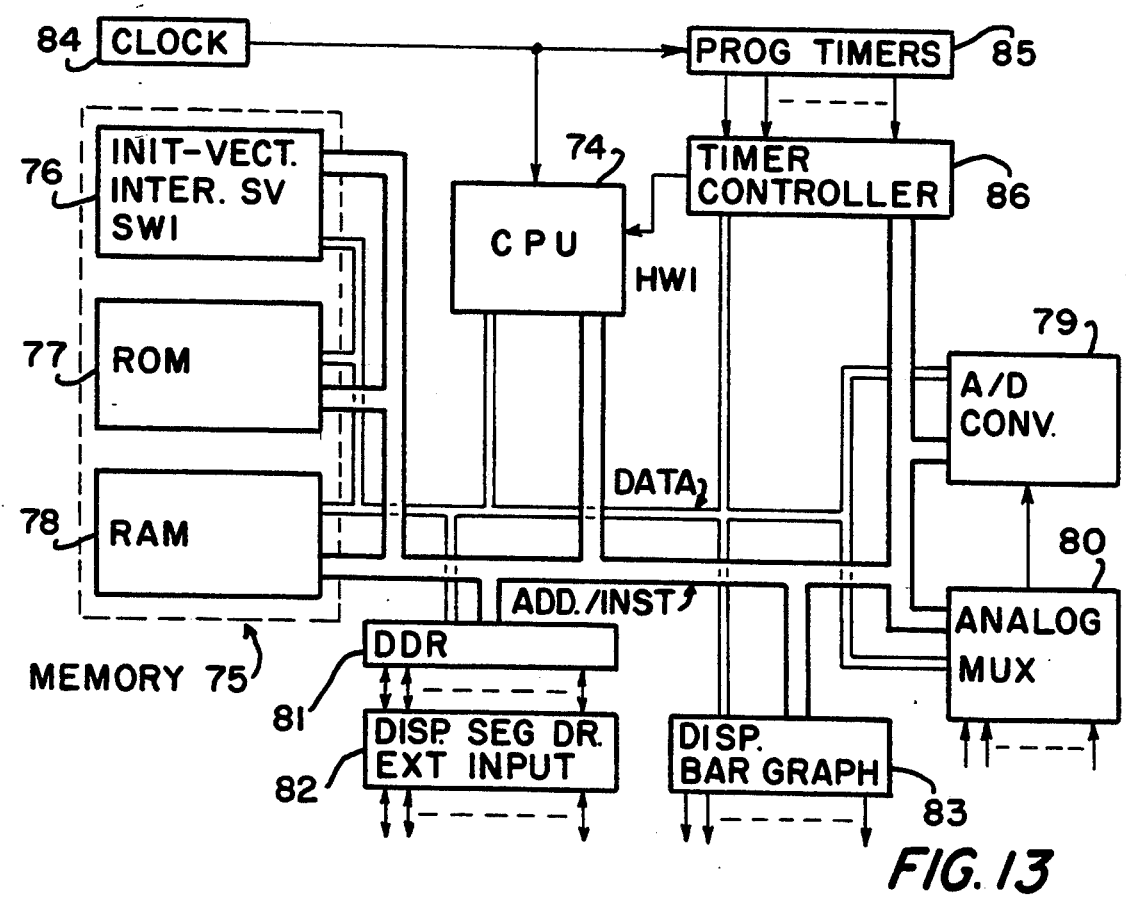
FIG. 13 is block diagram of one example of the computer contained in the third means of the vital signs monitor in accordance with the principles of the present invention.

Referring to FIG. 13, there is illustrated therein a general purpose computer that can be employed in the vital signs monitor in accordance with the principles of the present invention. This diagram is intended to describe the method of operation, data entry and display, plus program control, but it could take many other forms and still meet the instrument objectives.

The CPU (central processing unit) 74 interprets instructions and sets up the data paths for data and external instructions, for single and multi byte as well as multiple clock cycle instructions. Additionally, unit 74 performs single arithmatic functions, i.e., adds, subtracts relationals, shifts plus logical comparison (OR, AND, EXCOR, etc.).

The main memory 75 contains three distinct sections.

1. Start up/interrupt unit 76. This unit has three stored programs, one for initializing, one for "cleaning up the stack" and loading the initializing vectors to run the initialization program. The other two programs are for servicing interrupts and for both hardware and software interrupts. They basically allow "saving the present state" prior to interrupt, providing an interrupt vector to a service routine and then an orderly return from the interrupt.

2. A ROM (read only in memory) 77. This units serves as program memory as well as holding look up tables (LUT)s and special routines to perform mathematical operations, logical operations (alarm processing) and is non alterable after written into once.

3. A RAM (random access memory) 78. This unit is a read-write memory which serves as the workspace for programs affording space for accumulators, tables and data storage as well as room for the downloaded alarm surface map. This memory 78 has a low power mode allowing data retention while the processor is idling (waiting).

The A/D CONV (analog/digital convertor) 79 in conjunction with the analog mux (multiplexer) 80 under program control selects analog signals to be converted to 8 bit-binary numbers ($\frac{1}{4}$% accuracy), i.e., temperatures, flows, battery voltages etc.

The DDR (data direction register) 81 and DISP. SEG. DR. (display segment drivers) 82 allows the inputting of data (down loading) from the programmer unit 54 of FIG. 9, such as alarm limits, alarm hypergeometric surfaces that consider variables (age, medication loading, pathologies, etc of the patient) as well as reading out of historical data from the device to display or print. When not connected to programmer unit 54, the DDR 81 allows it to drive the segmented elements of the digital displays.

The bar graph display unit 83 drives the elements of the bar graphs contained in unit 44 of FIG. 8.

A real time clock 84 is coupled to the CPU 74 as well as to the programmable timers 85 which controls the timer controller 86 which controls the timing intervals to be established for collecting data, forming time averages etc. on a real time basis.

Referring to FIG. 14A, there is illustrated therein a flow chart of the basic operation of the computer of FIG. 13 and the major steps in program flow showing the real time stepping of the program. Subsequent figures give more detail on the blocks of FIG. 14A.

The real time run mode program of FIG. 14A is enabled automatically when it is plugged into the disposable unit, such as unit 19 in FIG. 8. A start vector 87 directs the program control to the initialize routine 88, clearing all data, starting counters (timers) then enters Start Exhale 89. The stepping or program advance is in intervals of ($t_i$) which provides from timers 85 of FIG. 13 the minimum measurement time interval (i.e. 50 msec.). $t_i$ allows the processor to perform certain routines which when completed returns the processor to the "Low Power Wait" (LPW) state 90.

After initialization, the processor enters "Start Exhale" 89 by reading the current value of $F_V$ as shown in curve 91 of FIG. 14B and comparing it to a prior $F_{V1}$ value by subtracting $F_V - F_{V1}$ to see if it exceeds a threshold. If it exceeds the threshold 92, exhale has started and the program moves forward. If $F_V$ didn't exceed the threshold, the program stores $F_V$ in 93 and goes into LPW 90 to wait for the next $t_i$.

In actual processing, if the threshold is exceeded it might be checked several times to make sure that $F_V$ was not a false start.

After leaving Start Exhale 89, the computer checks to see if the first pass flag 94 is set indicating the beginning of operation and possibly the program started during exhale. If the flag is set, the program executes but does not accumulate data, clears the first pass flag 94 and sets the second pass flag 95. On the second pass, after exiting Stored History Data 96, the first pass flag 94 is cleared and the second pass flag 95 is set indicating a valid start of exhale, but invalid data from the previous exhale, so it clears second pass flag 95 and again bypasses the calibration of tidal volume, minute volume, and respiration rate from the previous breath. On the next pass, (third entry) the computer will assume normal operation.

In normal operation, block 97 compares the present time $t_p$ with the stored $t_s$ by subtracting $t_p - t_s$ to determine $\Delta t_B$, the breath interval ($1/\Delta t_B = RR$). The computer then calculates from the prior breaths data tidal volume, respiration rate, $=(1/\Delta t_B)$, $O_2$, $MV = (TV)/\alpha t_B$. Note, more elaborate routines for minute volume can be used by storing many values of TV and $\Delta t_B$ to predict present minute volumes and future minute volumes (trending analysis).

After completing the operation in block 97, the alarm processor routines 98 are entered to determine if an alarm condition exists at 99, in the most complex case, based on patient statistics, medication loading, and vital signs, and, in the simplest form, based on exceeding individual (one or more) preset alarm thresholds.

After completing the alarm routines, the computer enters "Integrate Tidal Volume" loop 100.

The "Measurement and Display Flow" 101 causes the analog multiplexer to select $F_V$, convert and to latch it and display the present value on a bar graph 102. The values of $\Delta F_V$, $T_{EX}$, and $T_{O2}$ are converted at 103 and corrected with the look up tables. Once completed, "Calc & Sto" 104 is entered which uses previously described relationships to calculate $P_{o2}$ (t), % $O_2$ (t), % $CO_2$ (t), etc. and add them to the accumulator register 105.

Once this processing is complete, the computer enters "End of Exhale" 106 and like "Start of Exhale" 89 compares $F_{V1}$, (that initialized "Start of Exhale") with the present $F_V$, $F_{V1} - F_V < L$. Again multiple loops can be used to assure "End of Exhale". If its not the end of exhale as indicated by 107, the processor assumes the LPW state at 108 waiting for the next $T_i$.

If it is the end of exhale, the processor checks the battery at 109 and, if it is determined good at 110, the processor clears the accumulator 105 and enters current data into the historical data memory 96 (FIFO) with a time of entry stored with the data from programmable timers 85 of FIG. 13.

The processor then proceeds to "Start Up Inhale" 89 to repeat the cycle.

The battery check routine 109 will be described further with the aid of FIGS. 15 and 16.

When the disposable unit is connected to battery 20 of the disposable unit of FIG. 4A which is also shown in FIG. 15, battery 20 supplies the power to the processor and charges the reference battery 111 in the processor unit which maintains vectors and some data when not in use. The reference battery 111 is also used for the analog to digital reference supply. A voltage divider 112 provides a voltage $V_{DD}$ (K)/K+1 that will drop in value with the battery voltage. When the batteries are fully charged $V_{DD} > V_{DD}$ (K/K+1) > $V_{REF}$.

Figure 16:
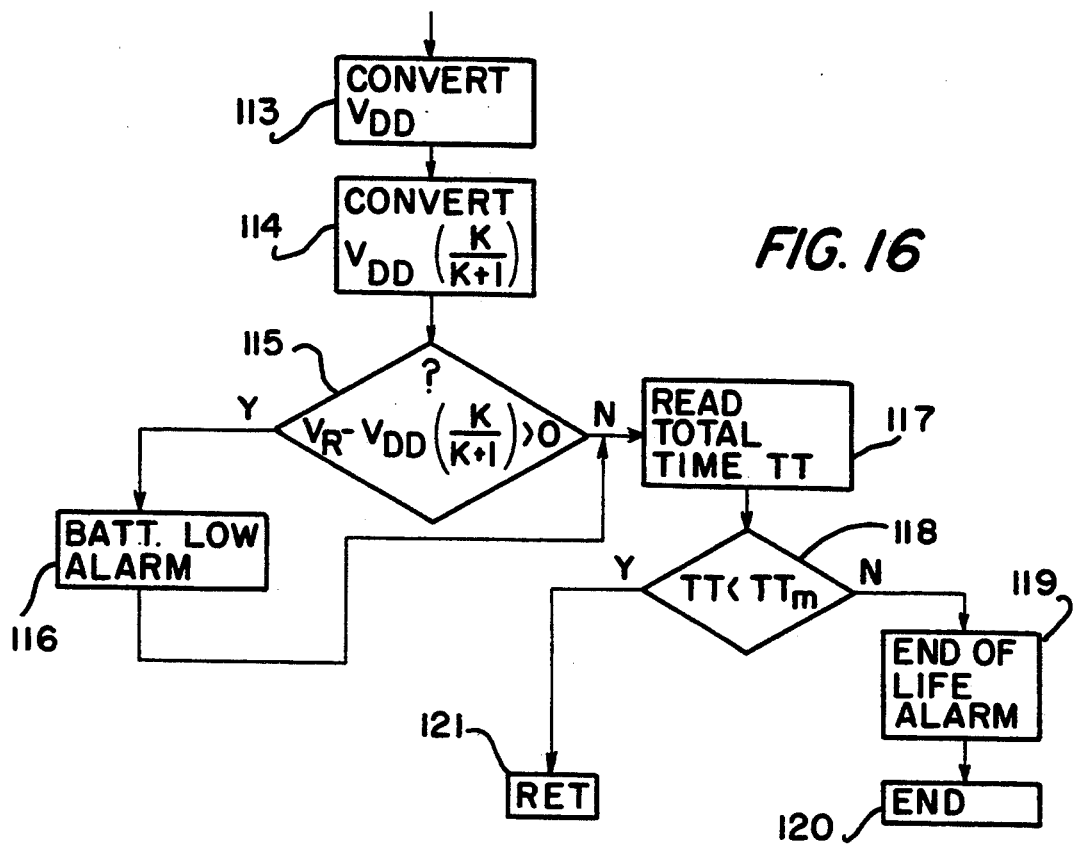
FIG. 16 is a flow diagram of the battery checking circuit in the flow diagram of FIG. 14.

The processor in order to determine the state of charge of the battery employs the flow chart shown in FIG. 16. Block 113 converts a value of $V_{DD}$ and the value of $V_{DD}$ (K)/K+1 at 114 to digital and subtracts them $V_R - V_{DD}$ (K)/K+1 at 115. If the difference is less than 0 the battery is low and the processor enables the "Battery Low Alarm" at 116 and then reads the total time the processor has been used at 117. If this total time exceeds the expected life value $TT_m$ at 118, which depends on connector usage and life of battery 111, the "End of Life" alarm 119 is sounded which lasts for a preset time then clears a fusible link 120 in the hardware ending its useful life.

If $TT_m$ is not exceeded, a return is made to the main program via 121.

Figures 17, 18:
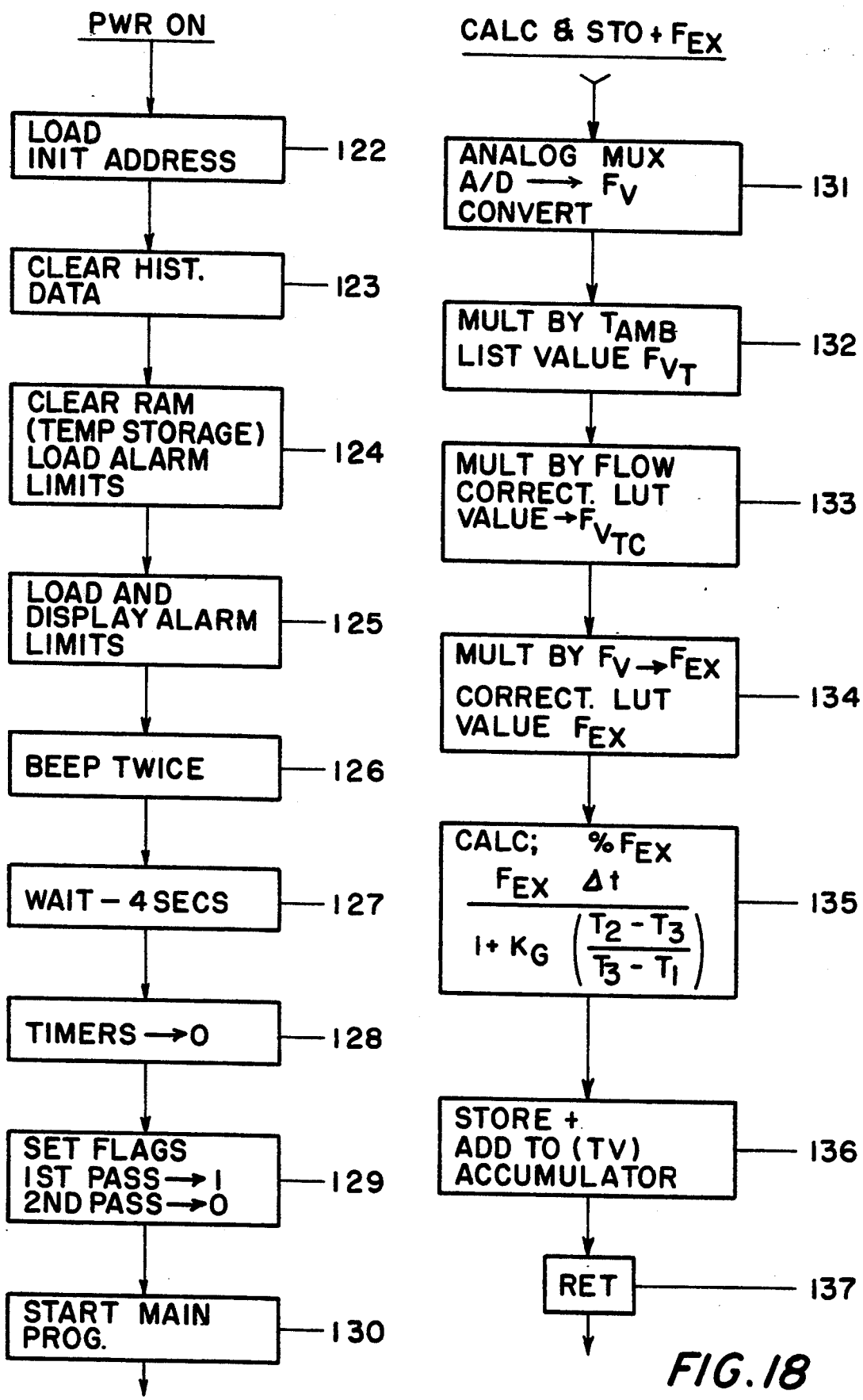
FIG. 17 is a flow diagram of the initialization block of FIG. 14.
FIG. 18 is a flow diagram useful in explaining the operation of the alarm system of the vital signs monitor in accordance with the principles of the present invention.

Referring to FIG. 17, the initialization routine is illustrated and it starts with "PWR On" causing the initialization vector to initialize the processor and point to the initialization routine 122. Routine 122 clears the historical data 123 from previous uses. 124 clears all RAM spaces (other then recently programmed alarm limits) and down loads alarm limits as illustrated in 125. If alarm limits have not been programmed, default values are provided from ROM 77 of FIG. 13.

Step 125 takes the alarm limits and loads and displays them for the user. The step 126 causes an audible sound to alert the user that alarm limits are being displayed. A waiting time period is provided by 127 allowing the operator time to read the alarm values. After the waiting period, the programmable timers 85 are reset at 128 through the timer control 86 other than time of year if it has been recently programmed in via the programmer 54 of FIG. 6, and "Usage Time". The next step at 129 is to set the first pass flag to one and the second pass flag to zero, then program control is turned over to the main program at 130.

An example of a measured variable that is integrated while being sampled at a rate of $t_i$ is shown in FIG. 18. The variable is % $F_{EX}(t)$, the value of the instantaneous portion of the flow leaving device 19 of FIG. 8, the sum being tidal volume.

Step 131 causes the analog multiplexer 80 of FIG. 13 to select $F_V$ and the analog to digital converter 79 of FIG. 13 provides an 8 bit-binary number. Step 132 enters the "$T_{AMB}$" look up table at the converted value and provides a multiplier for ambient temperature correction. The corrected value is then entered into the flow correction look up table at 133 and a multiplier provided, and the variable is multiplied by it. Step 134 provides the final correction factor that relates the corrected venturi flow to the main stream flow. Once corrected, step 135 calculates the percent of flow, by reading "fresh" values of $T_3$ and $T_1$ and making the calculations. Step 136 adds the interval value to tidal volume accumulator 100 of FIG. 14A. Step 137 returns the calculator or processor to its main program.

A very significant aspect of the vital signs monitor of the present invention is the alarm processing capability. Clearly, for individual alarms, i.e., oxygen, carbon dioxide, tidal volume, minute volume, heart rate, cardiac output etc., setting single alarm points or threshold values affords the patient a degree of protection. The levels these alarm points set relates to several patient variables, such as medications, age, pathologies, size, etc., and in many cases each measured variable will need two alarm points, high and low, i.e., a patient with bradycardia (low heart rate) being given medications to stimulate the heart rate, needs to be monitored on the low side in the event he does not respond to the medication and experiences continued degradation of his condition. Conversely, if he over responds to the medication, tachycardia, he should be monitored on the high side.

The alarm system of the present invention associated with the vital sign monitor measures several parameters concurrently and stores a record of their values as a function of time. With this information, the first and second derivatives (or higher) can be calculated by parametizing the data with the time of the measurement and the use of difference equations.

This provides the unit with a data base consisting of time series of data as well as higher derivatives of the time series of all the variables.

It is one of the objectives of the vital signs monitor of the present invention to deal with alarm situations where a threat to a patient exists based on measured values, although none of the individual values have exceeded their individual limits.

It is a further object of the vital signs monitor of the present invention when configured as shown in FIG. 9 at 51 to be capable of accepting inputs from other critical care monitoring systems or units, such as, tympanic, infra red thermometers, oximeters, sphignomanomometers, electro cardiograph, cardiac output, left ventricular ejection volume, etc.

Additional patient data, such as, age, sex, weight, surface area, pathology, medicinal loadings, can be entered via either being down loaded from a computer or being keyed in.

One of the objects of the alarm processing system associated with the vital signs monitor of the present invention is to determine combinations of measurements, both absolute and trend, that individually fail to reach the absolute alarm threshold, or the trend alarm threshold, but in combination clearly indicate an alarm condition.

Figure 19:
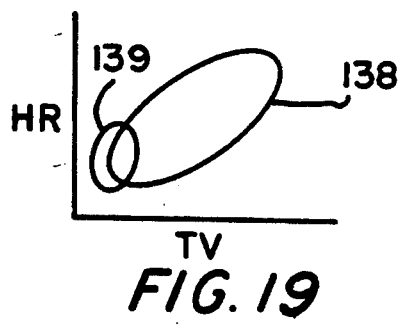
FIGS. 19, 20, 21, 22 and 23 are graphs employed in explaining the alarm threshold limits in accordance with the principles of the present invention.

Natural interrelations exist between measured variables. For example, with exercise heart rate and tidal volume positively correlate as shown in FIG. 19. For an adult population the region of correlation at 138 is large, while for an infant population, the region at 139 is small. The region outside the individual ellipses could be the alarm region, i.e., falling heart rate, climbing tidal volume.

Clearly, certain medications could cause shifts in the alarm regions for a specific patient and patient pathology, and these would be reflected in the shape of the alarm region.

Figure 20:
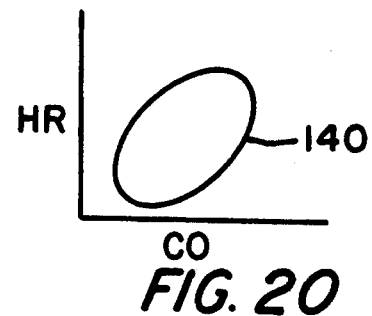

As another example, cardiac output (CO) (L/min.) (liters per minute) is related to the heart rate with a positive correlation as shown in FIG. 20 at 140 for certain individuals.

The scatter diagrams come from the underlying statistical distributions for cardiac output and heart rate for a specific type, i.e., male, 200 lbs., 2.5 $mtr^2$(meters) surface area and 50 years old, etc.

Figure 21:
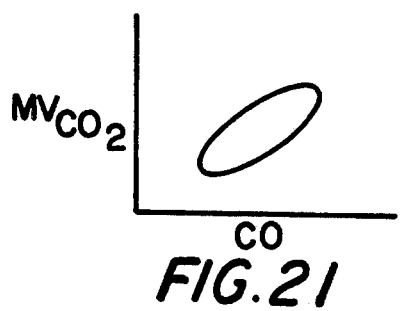
Figure 22:
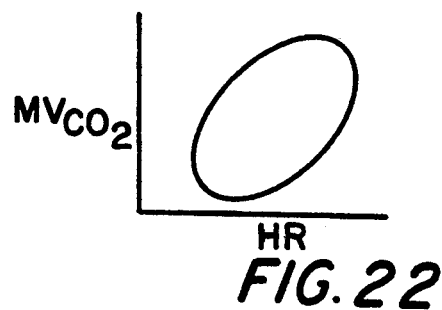

Minute volumes (mV) of carbon dioxide are also related to cardiac output (CO) as shown in FIG. 21. Again defining a region for a specific individual. Minute volumes of carbon dioxide can also correlate with heart rate as shown in FIG. 22.

Figure 23:
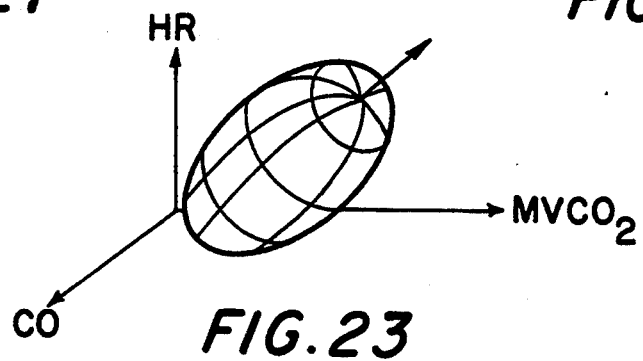

The three variables mutually correlate as shown in FIG. 23 with a three dimensional surface defining the alarm boundaries. These variables could be rates of change (trends) or absolute value.

Further, for example, considering age as a fourth parameter causing the surface to grow with the anatomical development, allows a method of establishing alarm values over an age range. To one skilled in the areas of probability and statistics, the growth of the diagram from a single variable distribution (one dimensional) to a scatter diagram (two dimensional), to a three dimensional surface as shown in FIG. 23 can be continued on a continuous basis in hyperdimensions of arbitrary degree, and can be mathematically characterized "N" dimensional surfaces. These surfaces acting as multidimensional alarm surfaces allows alarms to be generated earlier in the onset of a pathological disorder, affording an early warning to allow interventional therapies to be applied in a safer environment.

Also this type of alarm system can be used as a diagnostic tool in that data and data trends for certain pathologies define the disorder, as is common with heart and pulmonary function disorders.

The generation of the surfaces can come from two primary areas; (1) existing medical knowledge of known pathologies and their relationship with data associated with human vital signs that is used to train the equipment, such as is encountered in expert systems associated with the insurance industry; (2) self learning whereby the equipment is monitoring multiparameters, and an event occurs that can be medically characterized.

A data and trend analysis is made as a time series leading up to the event and the equipment remembers it, and during subsequent similar data analysis in the same environment it "warns" that a correlation exists with a prior event. If statistical significance can be attached to the particular event through several similar episodes, it is entered as part of the alarm surface, providing the diagnosis when the alarm sounds.

While we have described above the principles of our invention in connection with specific apparatus, it is to be clearly understood that this description is made only by way of example and not as a limitation to the scope of our invention as set forth in the object thereof and in the accompanying claims.

We claim:

1. A vital signs monitor comprising:
   first means adopted to be disposed at a selected location on a patient to pass at least exhaled gases therethrough;
   second means coupled to said first means to perform a plurality of resistive measurements of certain predetermined parameters of said exhaled gases and a plurality of optical absorption measurements of other predetermined parameters of said exhaled gases; and
   third means coupled to said second means responsive to said plurality of resistive measurements and said plurality of optical absorption measurements to provide individual read outs of at least a value of carbon dioxide in said exhaled gases, a value of tidal volume of said exhaled gases and a value of a respiration rate of said patient.

2. A monitor according to claim 1, wherein said first means includes
   fourth means to measure changes in mass flow of blood associated with systolic and diastolic portions of said patient's heart beat,
   said fourth means being coupled to said third means to enable said third means to provide a read out of a heart rate of said patient.

3. A monitor according to claim 2, wherein said third means includes
   a computer to process said plurality of resistive measurements, said plurality of optical absorption measurements and said changes in mass flow of blood associated with said systolic and said diastolic portions of said patient's heart beat in accordance with a predetermined program to provide said read outs.

4. A monitor according to claim 3, wherein said second means includes at least
   a housing having a passageway therein to enable a flow of oxygen from an oxygen inlet to said patient and a flow of a combination of said oxygen and said exhaled gases from said patient and a venturi tube coupled to said passageway to predeterminedly control said flow of said combination of said oxygen and said exhaled gases in said passageway,
   a first temperature sensitive resistance means disposed in said passageway adjacent said inlet to measure a temperature of said oxygen at said inlet,
   a second temperature sensitive resistance means disposed in said passageway responsive to said combination of said oxygen and said exhaled gases to measure a temperature of said combination of said oxygen and said exhaled gases, and
   a third temperature sensitive resistance means disposed in said venturi tube to measure at least a flow rate of said combination of said oxygen and said exhaled gases in said housing,
   said first, second and third temperature sensitive resistance means performing said plurality of resistive measurements.

5. A monitor according to claim 4, wherein said second means further includes
   a first optical absorption detection means disposed in an operative relationship with said flow of said combination of said oxygen and said exhaled gases to measure a value of humidity present therein, and
   a second optical absorption detection means disposed in an operative relationship with said flow of said combination of said oxygen and said exhaled gases to measure a value of carbon dioxide present therein,
   said first and second optical absorption detection means performing said plurality of optical absorption measurements.

6. A monitor according to claim 5, wherein said second means further includes
   an electronic circuit means coupled to said third resistance means to raise a resistance value and, hence, a temperature value thereof above a temperature of said flow of said combination of said oxygen and said exhaled gases so that said resistance value is lowered in proportion to a cooling effect of said flow of said combination of said oxygen and said exhaled gases to enable detection of said flow rate.

7. A monitor according to claim 6, wherein said third means further includes
   fifth means for providing first alarms when predetermined threshold levels of said plurality of resistive measurements, said plurality of optical absorption measurements and said changes in mass flow of blood associated with said systolic and said diastolic portions of said patient's heart beat are exceeded and a second alarm when said predetermined threshold levels are not exceeded but a combination of said plurality of resistive measurements, said plurality of optical absorption measurements and changes in mass flow of blood associated with said systolic and said diastolic portions of said patient's heart beat exceed other predetermined criteria.

8. A monitor according to claim 3, wherein said second means includes at least
   a housing having a passageway therein to enable a flow of oxygen from an oxygen inlet to said patient and a flow of a combination of said oxygen and said exhaled gases from said patient,
   a first optical absorption detection means disposed in an operative relationship with said flow of said combination of said oxygen and said exhaled gases to measure a value of humidity present therein, and
   a second optical absorption detection means disposed in an operative relationship with said flow of said combination of said oxygen and said exhaled gases to measure a value of carbon dioxide present therein,
   said first and second optical absorption detection means performing said plurality of optical absorption measurements.

9. A monitor according to claim 8, wherein said third means further includes
   fifth means for providing first alarms when predetermined threshold levels of said plurality of resistive measurements, said plurality of optical absorption measurements and said changes in mass flow of blood associated with said systolic and said diastolic portions of said patient's heart beat are exceeded and a second alarm when said predetermined threshold levels are not exceeded but a combination of said plurality of resistive measurements, said plurality of optical absorption measurements and said changes in mass flow of blood associated with said systolic and said diastolic portions of said patient's heart beat exceed other predetermined criteria.

10. A monitor according to claim 1, wherein said first means includes
a selected one of a face mask, an endotracheal tube and a nasal-oral ventilation adaptor.

11. A monitor according to claim 10, wherein said nasal-oral ventilation adapter includes
an optical arrangement coupled to said third means and disposed in at least one nasal portion of said nasal-oral adapter, said optical arrangement including fourth means to transmit light through blood perfused tissue of a nasal passage containing said one nasal portion and fifth means to detect changes in said light transmitted through said blood perfused tissue to thereby detect a change in mass flow of blood associated with systolic and diastolic portions of said patient's heart rate which is displayed as a read out on said third means.

12. A monitor according to claim 11, wherein said third means includes
a computer having sixth means to process said plurality of resistive measurement, said plurality of optical absorption measurements and said change in mass flow of blood associated with said portions of said patient's heart beat in accordance with a predetermined program to provide said read outs.

13. A monitor according to claim 12, wherein said computer further includes seventh
means to provide first alarms when predetermined threshold levels of said plurality of resistive measurements, said plurality of optical absorption measurements and said change in mass flow of blood associated with said portions of said patient's heart beat are exceeded and a second alarm when said predetermined threshold levels are not exceeded but a combination of said plurality of resistive measurements, said plurality of optical absorption measurements and said change in mass flow of blood associated with said portions of said patient's heart beat exceed other predetermined criteria.

14. A monitor according to claim 10, further including
a source of a selected one of dry air, moist air, oxygen and oxygen plus nitrogen;
said selected one of a face mask, an endotracheal tube and a nasal-oral ventilation adapter coupled to said source to enable administration of said selected one of dry air, moist air, oxygen and oxygen plus nitrogen to said patient;
said second means measuring a value of an unbreathed portion of said selected one of dry air, moist air, oxygen and oxygen plus nitrogen in said exhaled gases; and
said third means providing a read out of said value of said unbreathed portion of said selected one of dry air, moist air, oxygen and oxygen plus nitrogen in said exhaled gases.

15. A monitor according to claim 1, wherein said second means includes at least
a housing having a passageway therein to enable a flow of oxygen from an oxygen inlet to said patient and a flow of a combination of said oxygen and said exhaled gases from said patient and a venturi tube coupled to said passageway to predeterminedly control said flow of said combination of said oxygen and said exhaled gases in said passageway,
a first temperature sensitive resistance means disposed in said passageway adjacent said inlet to measure a temperature of said oxygen at said inlet,
a second temperature sensitive resistance means disposed in said passageway responsive to said combination of said oxygen and said exhaled gases to measure a temperature of said combination of said oxygen and said exhaled gases, and
a third temperature sensitive resistance means disposed in said venturi tube to measure at least a flow rate of said combination of said oxygen and said exhaled gases in said housing,
said first, second and third temperature sensitive resistance means performing said plurality of resistance measurements.

16. A monitor according to claim 15, wherein said second means further includes
a first optical absorption detection means disposed in an operative relationship with said flow of said combination of said oxygen and said exhaled gases to measure a value of humidity present therein, and
a second optical absorption detection means disposed in an operative relationship with said flow of said combination of said oxygen and said exhaled gases to measure a value of carbon dioxide present therein,
said first and second optical absorption detection means performing said plurality of optical absorption measurements.

17. A monitor according to claim 16, wherein said second means further includes
an electronic circuit means coupled to said third resistance means to raise a resistance value and, hence, a temperature value thereof above a temperature of said flow of said combination of said oxygen and said exhaled gases so that said resistance value is lowered in proportion to a cooling effect of said flow of said combination of said oxygen and said exhaled gases to enable detection of said flow rate.

18. A monitor according to claim 17, wherein said third means further includes
fourth means for providing first alarms when predetermined threshold levels of said plurality of resistive measurements and said plurality of optical absorption measurements are exceeded and a second alarm when said predetermined threshold levels are not exceeded but a combination of said plurality of resistive measurements and said plurality of optical absorption measurements exceed other predetermined criteria.

19. A monitor according to claim 1, wherein said second means includes at least
a housing having a passageway therein to enable a flow of oxygen from an oxygen inlet to said patient and a flow of a combination of said oxygen and said exhaled gases from said patient,
a first optical absorption detection means disposed in an operative relationship with said flow of said combination of said oxygen and said exhaled gases to measure a value of humidity present therein, and
a second optical absorption detection means disposed in an operative relationship with said flow of said combination of said oxygen and said exhaled gases to measure a value of carbon dioxide present therein, said first and second optical absorption detection means performing said plurality of optical absorption measurements.

20. A monitor according to claim 1, wherein said third means further includes fourth means for providing first alarms when predetermined threshold levels of said plurality of resistive measurements and said plurality of optical absorption measurements are exceeded and a second alarm when said predetermined threshold levels are not exceeded but a combination of said plurality of resistive measurements and said plurality of optical absorption measurements exceed other predetermined criteria.

21. A monitor according to claim 1, wherein said third means further includes fourth means responsive to given ones of said value of carbon dioxide, said value of tidal volume and said value of respiration rate to calculate at least cardiac output of said patient.

22. A monitor according to claim 1, wherein said third means further includes fourth means for enabling playing back historical values of at least said carbon dioxide, said tidal volume, said respiration rate and other predetermined data obtained previously from said patient.

23. A monitor according to claim 1, further including predetermined critical care monitor means, coupled to said third means, for delivering data to said third means, said critical care monitor means including selected ones of tymphanic monitors, infra red thermometers, oximeters, sphignomanometers, electro cardiographs, cardiac output monitors, and left ventricular injection volume monitors.

* * * * *